United States Patent
Furuya

(10) Patent No.: US 12,070,267 B2
(45) Date of Patent: Aug. 27, 2024

(54) OPHTHALMIC DEVICE, CONTROL METHOD OF OPHTHALMIC DEVICE, AND PROGRAM STORAGE MEDIUM

(71) Applicant: NIKON CORPORATION, Tokyo (JP)

(72) Inventor: Shunsuke Furuya, Kumagaya (JP)

(73) Assignee: NIKON CORPORATION, Tokyo (JP)

( * ) Notice: Subject to any disclaimer, the term of this patent is extended or adjusted under 35 U.S.C. 154(b) by 557 days.

(21) Appl. No.: 17/032,397

(22) Filed: Sep. 25, 2020

(65) Prior Publication Data

US 2021/0121058 A1 Apr. 29, 2021

(30) Foreign Application Priority Data

Sep. 26, 2019 (JP) .................................. 2019-175890

(51) Int. Cl.
*A61B 3/00* (2006.01)
*A61B 3/10* (2006.01)
(52) U.S. Cl.
CPC .......... *A61B 3/0091* (2013.01); *A61B 3/0008* (2013.01); *A61B 3/10* (2013.01)
(58) Field of Classification Search
CPC ........ A61B 3/0091; A61B 3/0008; A61B 3/10
USPC .......................................... 351/211, 212, 214
See application file for complete search history.

(56) References Cited

U.S. PATENT DOCUMENTS

| 2014/0293227 A1* | 10/2014 | Yoshida | A61B 3/0091 351/221 |
| 2016/0045107 A1* | 2/2016 | Welscher | A61B 3/0025 351/205 |
| 2016/0183859 A1* | 6/2016 | Hartung | A61B 5/14546 600/321 |
| 2017/0231489 A1* | 8/2017 | Fujimori | A61B 3/0091 351/206 |
| 2017/0231492 A1* | 8/2017 | Sudo | A61B 3/1015 351/206 |
| 2017/0238798 A1* | 8/2017 | Isogai | A61B 3/1005 |

FOREIGN PATENT DOCUMENTS

| JP | 2016077506 A | * | 5/2016 | ............... A61B 3/10 |
| JP | 2016-158721 A | | 9/2016 | |
| JP | 2018-038687 A | | 3/2018 | |

OTHER PUBLICATIONS

Office Action issued in corresponding Japanese Patent Application No. 2023-188702, dated Jun. 25, 2024, with English translation (5 pages).

* cited by examiner

*Primary Examiner* — Sharrief I Broome
(74) *Attorney, Agent, or Firm* — FOLEY & LARDNER LLP

(57) ABSTRACT

An ophthalmic device including a scanning optical system configured to scan an examined eye with light from a light source, a fixation light source configured to illuminate fixation light onto the examined eye through the scanning optical system so as to function as a fixation target, and a fixation light scanning section configured to scan the fixation light synchronized to scanning of the scanning optical system such that an illuminated fixation target does not move a specific distance or greater due to scanning of the scanning optical system.

5 Claims, 18 Drawing Sheets

OPHTHALMIC DEVICE, CONTROL METHOD OF OPHTHALMIC DEVICE, AND PROGRAM STORAGE MEDIUM

CROSS-REFERENCE TO RELATED APPLICATION

This application claims priority from Japanese Patent Application No. 2019-175890 filed on Sep. 26, 2019, the disclosure of which is incorporated by reference herein in its entirety.

BACKGROUND

Field of the Invention

The present disclosure relates to an ophthalmic device, to a control method of an ophthalmic device, and to a program storage medium.

Related Art

Japanese Patent Application Laid-Open (JP-A) No. 2016-158721 discloses an ophthalmological imaging device provided with plural light sources as fixation targets for changing a gaze direction of an examined eye, and in which the light source is switched to one of the plural light sources to present a fixation target to the examined eye.

However, there are installation location limitations of a fixation optical system for presenting the fixation targets.

SUMMARY

An ophthalmic device according to the present disclosure includes a scanning optical system configured to scan an examined eye with light from a light source, a fixation light source configured to illuminate fixation light onto the examined eye through the scanning optical system so as to function as a fixation target, and a fixation light scanning section configured to scan the fixation light synchronized to scanning of the scanning optical system such that an illuminated fixation target does not move a specific distance or greater due to scanning of the scanning optical system.

A control method of an ophthalmic device of the present disclosure is a control method of an ophthalmic device for controlling an ophthalmic device that includes a scanning optical system configured to scan an examined eye with light from a light source, a fixation light source configured to illuminate fixation light onto the examined eye through the scanning optical system so as to function as a fixation target, and a fixation light scanning section configured to scan the fixation light synchronized to scanning of the scanning optical system such that a fixation target illuminated on the examined eye does not move a specific distance or greater due to scanning of the scanning optical system. The control method of the ophthalmic device includes processing to control the fixation light source and the fixation light scanning section based on instruction information indicating an instruction to guide an orientation of the examined eye by controlling in such a manner that a fixation target is illuminated by the fixation light at a position corresponding to the instruction.

A non-transitory program storage medium of the present disclosure is a non-transitory storage medium stored with a program to cause fixation control processing to be executed by a processor. The processing is performed on an ophthalmic device including a scanning optical system configured to scan an examined eye with light from a light source, a fixation light source configured to illuminate fixation light onto the examined eye through the scanning optical system so as to function as a fixation target, and a fixation light scanning section configured to scan the fixation light synchronized to scanning of the scanning optical system such that a fixation target illuminated on the examined eye does not move a specific distance or greater due to scanning of the scanning optical system. The fixation control processing also includes controlling the fixation light source and the fixation light scanning section based on instruction information indicating an instruction to guide an orientation of the examined eye by controlling in such a manner that a fixation target is illuminated by the fixation light at a position corresponding to the instruction.

BRIEF DESCRIPTION OF THE DRAWINGS

Exemplary embodiments of the present disclosure will be described in detail based on the following figures, wherein.

DETAILED DESCRIPTION

Figure 1:
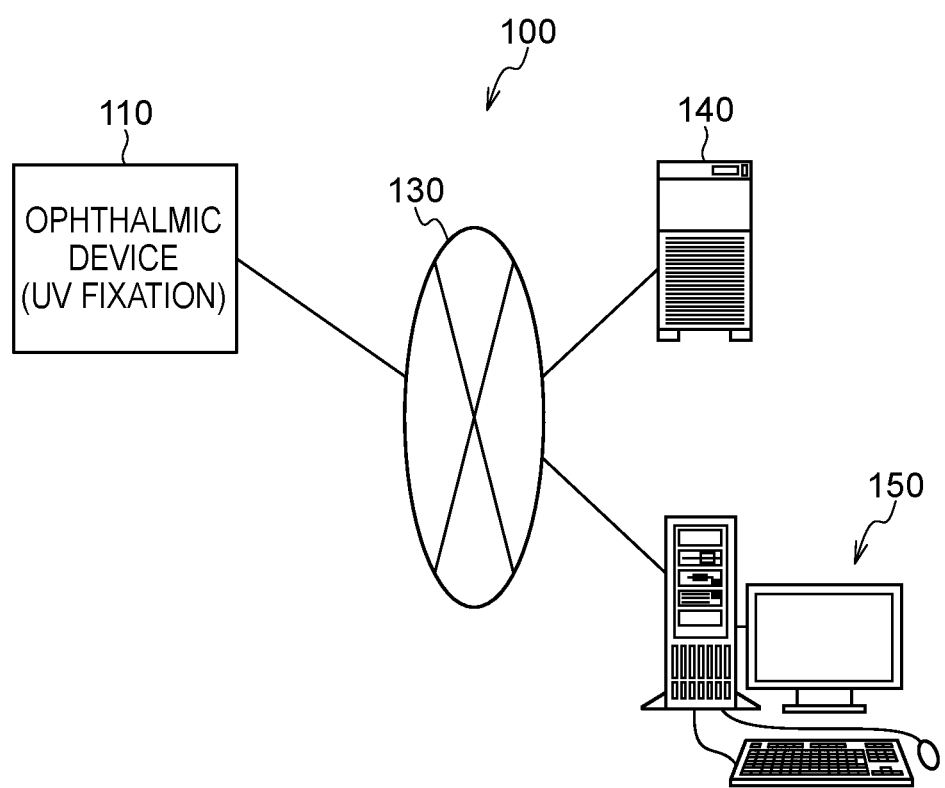
FIG. 1 is a block diagram illustrating an example of an ophthalmic system.

Detailed explanation follows regarding exemplary embodiments of the present disclosure, with reference to the drawings. Note that configuration elements and processing performing the same action or functioning in the same manner are appended with the same reference numeral throughout the drawings, and sometimes duplicate explanation will be omitted thereof.

Configuration of an ophthalmic system 100 will now be explained with reference to FIG. 1. As illustrated in FIG. 1, the ophthalmic system 100 includes an ophthalmic device 110, a server device (referred to hereafter as "server") 140, and an image display device (referred to hereafter as "viewer") 150. The ophthalmic device 110 acquires fundus images. The server 140 stores plural fundus images obtained by imaging the fundus of plural patients using the ophthalmic device 110, and stores these in association with patient IDs. The viewer 150 displays the fundus images acquired from the server 140.

The ophthalmic device is an example of an "ophthalmic device" of the present disclosure.

The ophthalmic device 110, the server 140, and the viewer 150 are coupled together over a network 130.

Figure 2:
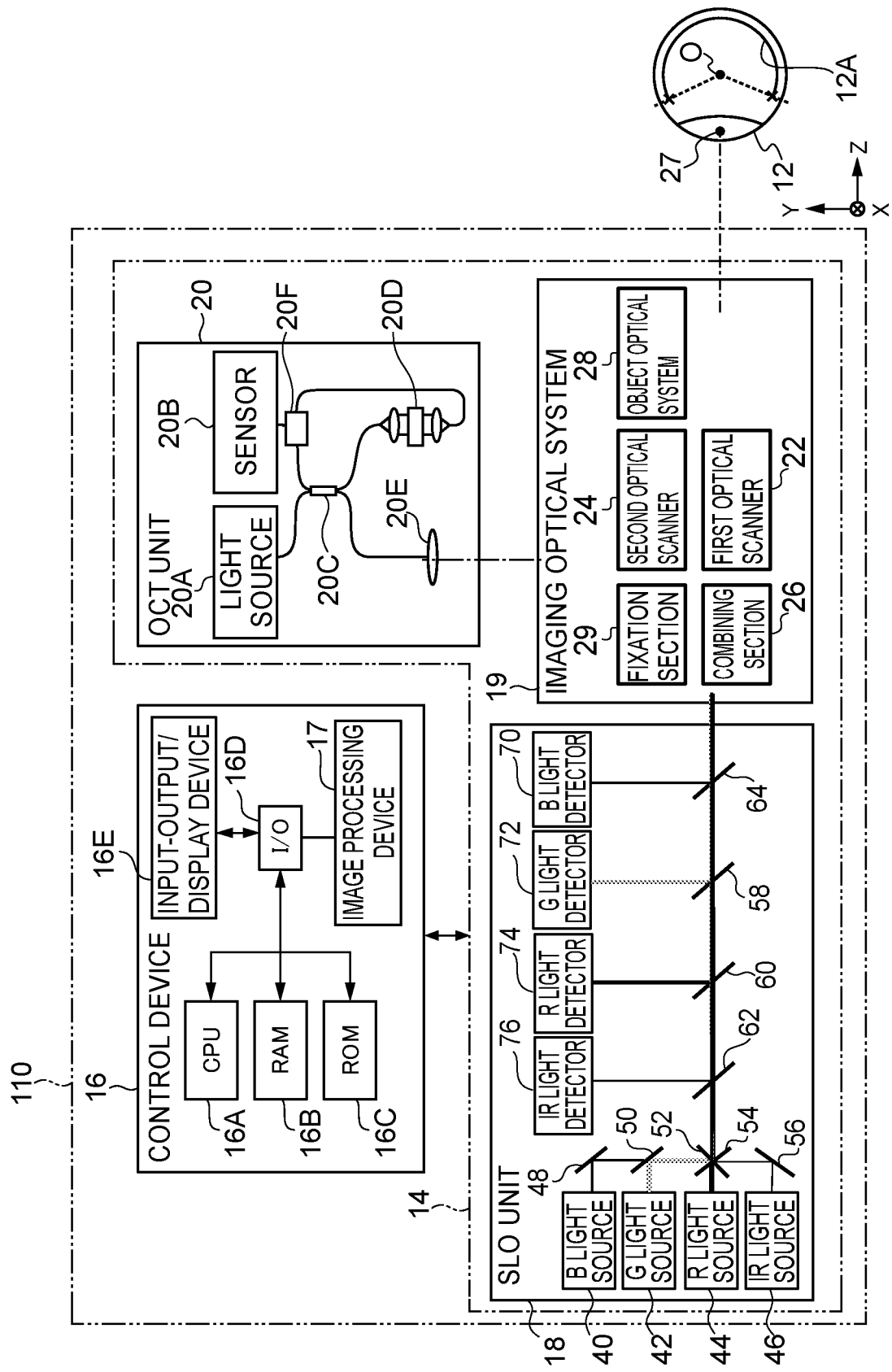
FIG. 2 is a schematic configuration diagram illustrating an example of an overall configuration of an ophthalmic device.

Explanation follows regarding configuration of the ophthalmic device 110, with reference to FIG. 2.

For ease of explanation, scanning laser ophthalmoscope is abbreviated to SLO, and optical coherence tomography is abbreviated to OCT.

In cases in which the ophthalmic device 110 is installed on a horizontal plane with a horizontal direction taken as an X direction, a direction perpendicular to the horizontal plane is denoted as being a Y direction, and a direction connecting the center of the pupil at an anterior eye portion of the examined eye 12 and the center of the eyeball is denoted as being a Z direction. The X direction, the Y direction, and the Z direction are thus mutually perpendicular directions.

The ophthalmic device 110 includes an imaging device 14 and a control device 16. The imaging device 14 is provided with an SLO unit 18, an OCT unit 20, and an imaging optical system 19, and acquires a fundus image of the fundus of the examined eye 12. Two-dimensional fundus images that have been acquired by the SLO unit 18 are referred to hereafter as SLO images. Tomographic images, face-on images (en-face images) and the like of the fundus (for example the retina) created based on OCT data acquired by the OCT unit 20 are referred to as OCT images.

The imaging device 14 is an example of an "imaging section" of the present disclosure. The control device 16 is an example of a "control section" of the present disclosure.

The control device 16 includes a computer provided with a Central Processing Unit (CPU) 16A, which is an example of a processor, Random Access Memory (RAM) 16B, Read-Only Memory (ROM) 16C, and an input/output (I/O) port 16D.

The control device 16 is provided with an input/display device 16E coupled to the CPU 16A through the I/O port 16D. The input/display device 16E includes a graphical user interface to display images of the examined eye 12 and to receive various instructions from a user. A touch panel display is an example of the graphical user interface.

The control device 16 is provided with an image processing device 17 coupled to the I/O port 16D. The image processing device 17 generates images of the examined eye 12 based on data acquired by the imaging device 14. Note that the control device 16 includes a communication I/F 16F connected to an I/O port 16D, and is coupled to the network 130 through the communication I/F 16F.

Although the control device 16 of the ophthalmic device 110 is, as described above, provided with the input/display device 16E as illustrated in FIG. 2, the present disclosure is not limited thereto. For example, a configuration may adopted in which the control device 16 of the ophthalmic device 110 is not provided with the input/display device 16E, and instead a separate input/display device is provided that is physically independent of the ophthalmic device 110. In such cases, the display device is provided with an image processing unit that operates under the control of the CPU 16A in the control device 16. Such an image processing unit may display SLO images and the like based on an image signal output as an instruction by the CPU 16A.

The imaging device 14 operates under the control of the CPU 16A in the control device 16. The imaging device 14 includes the SLO unit 18, the imaging optical system 19, and the OCT unit 20. The imaging optical system 19 includes a first optical scanner 22, a second optical scanner 24, a combining section 26, an objective optical system 28, and a fixation section 29. The first optical scanner 22, the second optical scanner 24, the combining section 26, the objective optical system 28, and the fixation section 29 are illustrated as functional blocks inside the imaging optical system 19.

The first optical scanner 22 scans incident light in one direction (for example the X direction), and the second optical scanner 24 scans the incident light in another direction (for example the Y direction). The first optical scanner 22 and the second optical scanner 24 thereby scan light emitted from the SLO unit 18 and light emitted from the OCT unit 20 two dimensionally, in the X direction and the Y direction. As long as the first optical scanner 22 and the second optical scanner 24 are optical elements capable of deflecting light beams, they may be configured by any out of, for example, polygon mirrors, galvanometer mirrors, or the like. A combination thereof may also be employed.

The combining section 26 combines the light from the SLO unit 18 and the light from the OCT unit 20. The objective optical system 28 emits light from the SLO unit 18 and light from the OCT unit 20 toward an examined eye 12. The fixation section 29 had the function of a fixation target to guide the orientation (gaze direction) of the examined eye 12.

The objective optical system 28 may be a reflection optical system employing a concave mirror such as an elliptical mirror, a diffraction optical system employing a wide-angle lens, or may be a reflection-diffraction optical system employing a combination of a concave mirror and a lens. Employing a wide-angle optical system that utilizes an elliptical mirror, wide-angle lens, or the like enables imaging of not only a central portion of the fundus to be performed, but also of the peripheral portion of the fundus.

For a system including an elliptical mirror, a configuration may be adopted that utilizes an elliptical mirror system as disclosed in International Publication (WO) Nos. 2016/103484 or 2016/103489. The disclosures of WO Nos. 2016/103484 and 2016/103489 are incorporated in their entirety by reference herein.

Examination of the fundus over a wide field of view (FOV) 12A is implemented by employing the imaging optical system 19. The FOV 12A refers to an imageable range by the imaging device 14. The FOV 12A may be expressed as a viewing angle. In the present exemplary embodiment the viewing angle may be defined in terms of an internal illumination angle and an external illumination angle. The external illumination angle is the angle of illumination by a light beam illuminated from the ophthalmic device 110 toward the examined eye 12, and is an angle of illumination defined with reference to a pupil 27. The internal illumination angle is the angle of illumination of a light beam illuminated onto the fundus, and is an angle of illumination defined with reference to an eyeball center O.

A correspondence relationship exists between the external illumination angle and the internal illumination angle. For example, an external illumination angle of 120° is equivalent to an internal illumination angle of about 160°. The internal illumination angle in the present exemplary embodiment is 200°. An imaging optical system 30 configured from such a wide-angle optical system has an ultra wide-angled field of view (FOV) on the fundus and enables imaging of a 200° internal illumination angle range of the fundus with the eyeball center as the origin. Namely, imaging is enabled for a region from a posterior pole portion of the fundus of the examined eye 12. Obviously the present disclosure is not limited to a wide-angle optical system, and application may made to an ophthalmic device equipped with various angle of view optical systems.

SLO fundus images obtained by imaging at an imaging angle of view having an internal illumination angle of 160° or greater are referred to as UWF-SLO fundus images. UWF is an abbreviation of ultra wide field.

An SLO system is realized by the control device 16, the SLO unit 18, and the imaging optical system 19 as illustrated in FIG. 2. The SLO system is capable of fundus imaging over the wide FOV 12A using the imaging optical system 19.

The SLO unit 18 is provided with a blue (B) light source 40, a green (G) light source 42, a red (R) light source 44, and an infrared (for example near infrared) (IR) light source 46. The SLO unit 18 is also provided with optical systems 48, 50, 52, 54, 56 to guide the light from the light sources 40, 42, 44, 46 onto a single optical path using transmission or reflection. The optical systems 48, 50, 56 are configured by mirrors, and the optical systems 52, 54 are configured by beam splitters. B light is reflected by the optical system 48, is transmitted through the optical system 50, and is reflected by the optical system 54. G light is reflected by the optical systems 50, 54, R light is transmitted through the optical systems 52, 54, and IR light is reflected by the optical systems 56, 52, such that the respective lights are guided onto a single optical path.

The SLO unit 18 is configured so as to be capable of switching between the light source or the combination of light sources employed to emit laser beams of different wavelengths, such as a mode in which G light, R light, and B light are emitted, a mode in which infrared light is emitted, and the like. Although the example in FIG. 2 includes four light sources, i.e. the blue (B) light source 40, the G light source 42, the R light source 44, and the IR light source 46, the present disclosure is not limited thereto. For example, the SLO unit 18 may, furthermore, also include a white light source, in a configuration in which light is emitted in various modes, such as a mode in which white light is emitted alone.

Light introduced to the imaging optical system 19 from the SLO unit 18 is scanned in the X direction and the Y direction by the first optical scanner 22 and the second optical scanner 24. The scanned light passes through the object optical system 28 and the pupil 27 and is illuminated onto a posterior eye portion of the examined eye 12. Reflected light that has been reflected by the fundus passes through the object optical system 28, the first optical scanner 22, and the second optical scanner 24, and is introduced into the SLO unit 18.

The anterior eye portion of the examined eye 12 is a section serving as an anterior eye segment including, for example, the cornea, the iris, the angle, the lens, the ciliary body, and a portion of the vitreous body. The posterior eye portion of the examined eye 12 is a section serving as a posterior eye segment including, for example, the remaining portion of the vitreous body, the retina, the choroid, and the sclera. Note that the anterior eye portion of the vitreous body is a section in the vitreous body at the cornea side of a boundary of an X-Y plane passing through a nearest point of the lens to the eyeball center, and the posterior eye portion of the vitreous body is a section in the vitreous body that is not the vitreous body of the anterior eye portion.

The SLO unit 18 is provided with a beam splitter 64 and a beam splitter 58. From out of the light coming from the posterior eye portion (for example the fundus) of the examined eye 12, the B light therein is reflected by the beam splitter 64 and light other than B light therein is transmitted by the beam splitter 64. From out of the light transmitted by the beam splitter 64, the G light therein is reflected by the beam splitter 58 and light other than G light therein is transmitted by the beam splitter 58. The SLO unit 18 is further provided with a beam splitter 60 that, from out of the light transmitted through the beam splitter 58, reflects R light therein and transmits light other than R light therein. The SLO unit 18 is further provided with a beam splitter 62 that reflects IR light from out of the light transmitted through the beam splitter 60. The SLO unit 18 is further provided with a B light detector 70 to detect B light reflected by the beam splitter 64, a G light detector 72 to detect G light reflected by the beam splitter 58, an R light detector 74 to detect R light reflected by the beam splitter 60, and an IR light detector 76 to detect IR light reflected by the beam splitter 62.

Light that has passed through the object optical system 28, the first optical scanner 22, and the second optical scanner 24 and been introduced into the SLO unit 18 (i.e. reflected light that has been reflected by the fundus) is, when B light, reflected by the beam splitter 64 and photo-detected by the B light detector 70, and when G light, passes through the beam splitter 64 and is reflected by the beam splitter 58 and photo-detected by the G light detector 72. When R light, the incident light is transmitted through the beam splitters 64, 58, reflected by the beam splitter 60, and photo-detected by the R light detector 74. When IR light, the incident light is transmitted through the beam splitters 64, 58, 60, reflected by the beam splitter 62, and photo-detected by the IR light detector 76. The image processing device 17 that operates under the control of the CPU 16A employs signals detected by the B light detector 70, the G light detector 72, the R light detector 74, and the IR light detector 76 to generate UWF-SLO images.

The UWF-SLO images include a UWF-SLO image (green fundus image) obtained by imaging the fundus in green, and a UWF-SLO image (red fundus image) obtained by imaging the fundus in red. The UWF-SLO images further include a UWF-SLO image (blue fundus image) obtained by imaging the fundus in blue, and a UWF-SLO image (IR fundus image) obtained by imaging the fundus in IR.

The control device 16 may control the light sources 40, 42, 44 so as to emit light at the same time as each other. The G fundus image, the R fundus image, and the B fundus image may be obtained at mutually corresponding positions by imaging the fundus of the examined eye 12 using B light, G light, and R light at the same time. An RGB color fundus image may be obtained from the G fundus image, the R fundus image, and the B fundus image. The control device 16 may also control the light sources 42, 44 so as to emit light at the same time as each other. The G fundus image and the R fundus image are obtained at mutually corresponding positions by imaging the fundus of the examined eye 12 using G light and R light at the same time in this manner. An RG color fundus image may be obtained from the G fundus image and the R fundus image.

In this manner, the UWF-SLO images are, specifically, the B fundus image, the G fundus image, the R fundus image, the IR fundus image, the RGB color fundus image, and the RG color fundus image. Respective image data for UWF-SLO images are sent, together with patient information input through the input/display device 16E, from the ophthalmic device 110 to the server 140 through the communication I/F 16F. The respective image data for the UWF-SLO images and the patient information is associated and stored in the storage device 254. Note that examples of the patient information include a patient ID, patient name, age, visual acuity, a right eye/left eye discriminator, eye axial length, and the like.

An OCT system is realized by the control device 16, the OCT unit 20, and the imaging optical system 19 illustrated in FIG. 2. The OCT system uses the imaging optical system 19 to enable fundus imaging to be performed over the wide FOV 12A similarly to when imaging the SLO fundus images as described above. The OCT unit 20 includes a light source 20A, a sensor (detector) 20B, a first light coupler 20C, a reference optical system 20D, a collimator lens 20E, and a second light coupler 20F.

Light emitted from the light source 20A is split by the first light coupler 20C. After one part of the split light has been collimated into parallel light by the collimator lens 20E, to serve as measurement light, the parallel light is introduced into the imaging optical system 19. The measurement light is scanned in the X direction and the Y direction by the first optical scanner 22 and the second optical scanner 24. The scanned light is illuminated onto the fundus through the object optical system 28 and the pupil 27. Measurement light that has been reflected by the fundus passes through the object optical system 28, the first optical scanner 22, and the second optical scanner 24 so as to be introduced into the OCT unit 20. The measurement light then passes through the collimator lens 20E and the first light coupler 20C before being incident to the second light coupler 20F.

The other part of the light emitted from the light source 20A and split by the first light coupler 20C is introduced into the reference optical system 20D as reference light, and is made incident to the second light coupler 20F through the reference optical system 20D.

The respective lights that are incident to the second light coupler 20F, namely the measurement light reflected by the fundus and the reference light, interfere with each other in the second light coupler 20F so as to generate interference light. The interference light is photo-detected by the sensor 20B. The image processing device 17 operating under the control of the CPU 16A generates OCT images, such as tomographic images and en-face images, based on OCT data detected by the sensor 20B.

OCT fundus images obtained by imaging at an imaging angle of view having an internal illumination angle of 160° or greater are referred to as UWF-OCT images.

Image data of the UWF-OCT images are sent, together with patient information, from the ophthalmic device 110 to the server 140 through the communication I/F 16F. The image data of the UWF-OCT images and the patient information are stored in a storage device 254.

Note that although in the present exemplary embodiment an example is given in which the light source 20A is a swept-source OCT (SS-OCT), the light source 20A may be from various OCT systems, such as from a spectral-domain OCT (SD-OCT) or from a time-domain OCT (TD-OCT) system.

Figure 3:
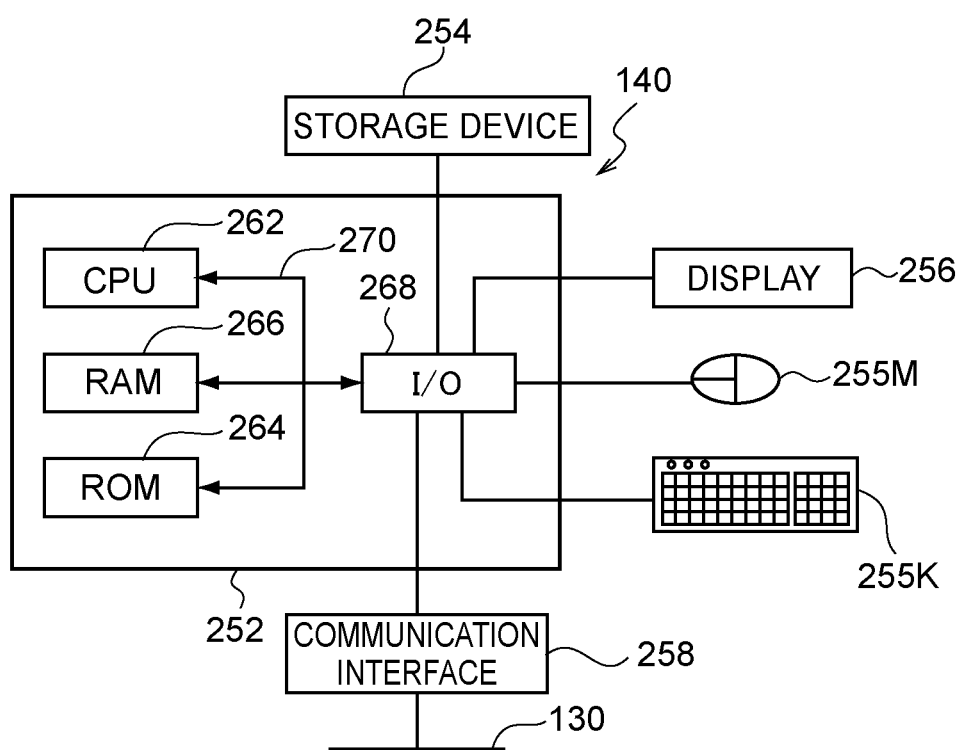
FIG. 3 is a block diagram illustrating an example of a configuration of an electrical system of a server.

Explanation follows regarding a configuration of an electrical system of the server 140, with reference to FIG. 3. As illustrated in FIG. 3, the server 140 is provided with a computer body 252. The computer body 252 includes a CPU 262, RAM 266, ROM 264, and an input/output (I/O) port 268, connected together through a bus 270. A storage device 254, a display 256, a mouse 255M, a keyboard 255K, and a communication interface (I/F) 258 are coupled to the input/output (I/O) port 268. The storage device 254 is, for example, configured by non-volatile memory. The input/output (I/O) port 268 is coupled to the network 130 through the communication interface (I/F) 258. The server 140 is thus capable of communicating with the ophthalmic device 110, and the viewer 150. The storage device 254 is stored with an imaging processing program, described later. Note that the imaging processing program may be stored in the ROM 264.

A processing section 208, described later, of the server 140 stores various data received from the ophthalmic device 110 in the storage device 254.

A configuration of an electrical system of the viewer 150 is similar to the configuration of the electrical system of the server 140 and so detailed explanation thereof will be omitted.

Figure 4:
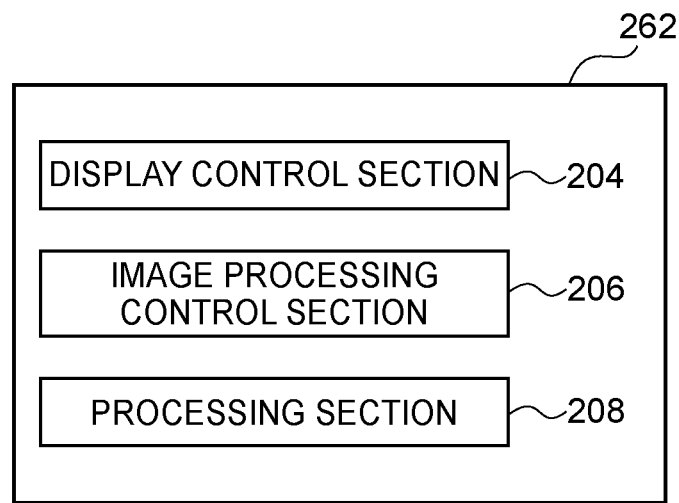
FIG. 4 is a block diagram illustrating an example of functionality of a server.

Explanation follows regarding various functions implemented by the CPU 262 of the management server 140 executing the image processing program, with reference to FIG. 4. The image processing program includes a specific display control function, a specific image processing control function, and a specific processing function. The CPU 262 functions as the display control section 204, the image processing control section 206, and the processing section 208, as illustrated in FIG. 4, by the CPU 262 executing the image processing program that includes these functions.

Figure 5:
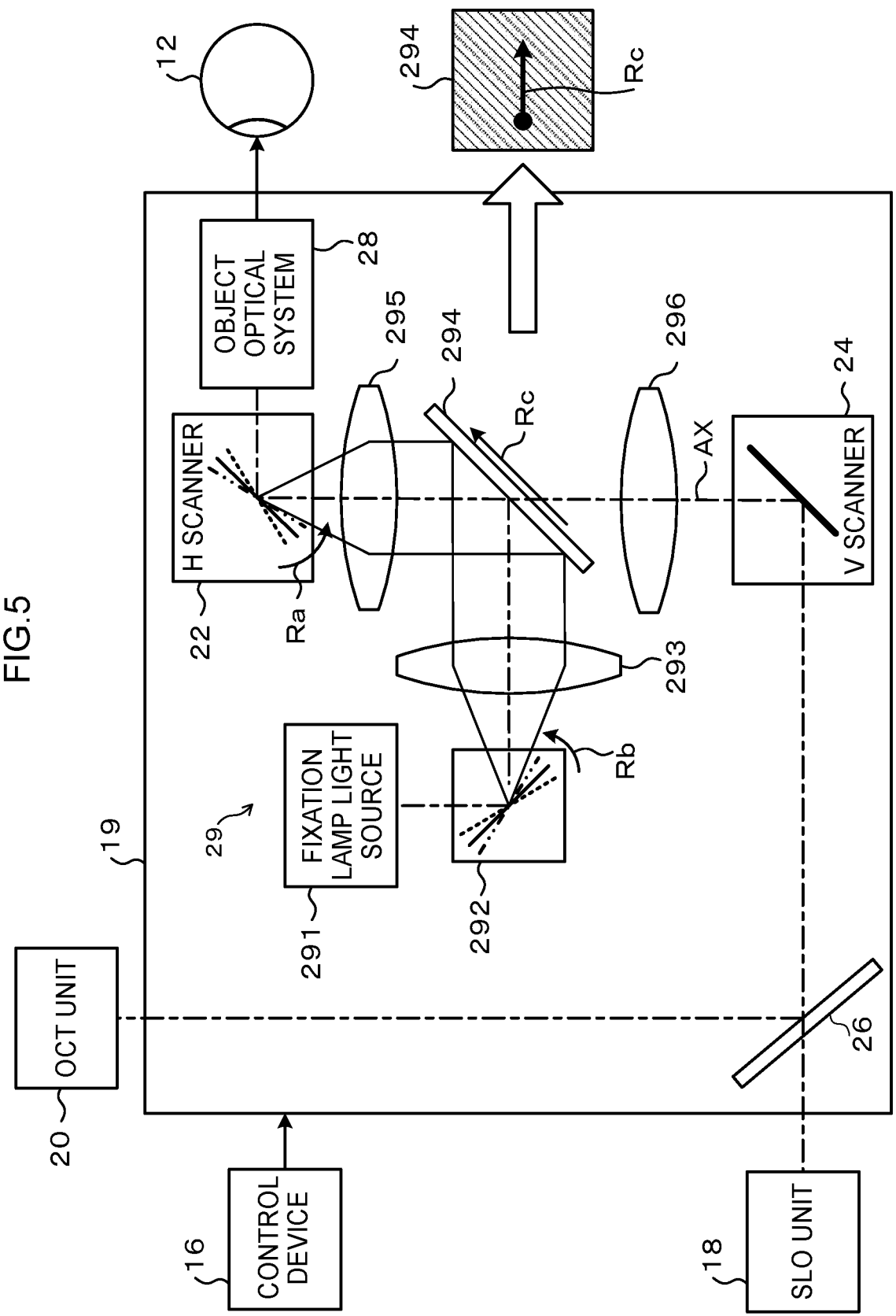
FIG. 5. is a schematic diagram illustrating an example of a schematic configuration of an imaging optical system.

Explanation next follows regarding a configuration of the imaging optical system 19 including the fixation section 29, with reference to FIG. 5. Note that light emitted from the SLO unit 18 and incident to the imaging optical system 19 is referred to below as "SLO light", and light emitted from the OCT unit 20 and incident to the imaging optical system 19 is referred to below as "OCT light". The present exemplary embodiment is configured such that the SLO light and the OCT light incident to the imaging optical system 19 are each formed by a substantially parallel beam.

FIG. 5 is a schematic diagram illustrating an example of a schematic configuration of the imaging optical system 19. As illustrated in FIG. 5, the imaging optical system 19 includes the combining section 26 for combining the SLO light and the OCT unit light, the first optical scanner 22 (labeled as H scanner in FIG. 5), the second optical scanner 24 (labeled as V scanner in FIG. 5), the object optical system 28, and the fixation section 29 that functions as a fixation target to guide the orientation (gaze direction) of the examined eye 12.

In the present exemplary embodiment, a dichroic mirror with wavelength dependency may be employed as the combining section 26. The combining section 26 has a function to combine the optical path of the SLO light toward the examined eye side with the optical path of the OCT toward the examined eye side. The combining section 26 also has a function to separate light that has been illuminated into the examined eye 12 and reflected at the examined eye 12 by separating into the optical path of the reflected light based on SLO light and the optical path of the reflected light based on the OCT light, and to guide the reflected light based on SLO light toward the SLO unit 18, and to guide the reflected light based on OCT light toward the OCT unit 20.

The light (SLO light or OCT light) emitted from the combining section 26 is introduced into the object optical system 28 through the first optical scanner 22 and the second optical scanner 24, and is emitted toward the examined eye 12 by the object optical system 28. A first lens group 295 on the first optical scanner 22 side and a second lens group 296 on the second optical scanner 24 side are disposed on the optical path between the first optical scanner 22 and the second optical scanner 24.

The optical system configured by the first lens group 295 and the second lens group 296 is an afocal optical system configured such that a position of the first optical scanner 22 (position of a scanning center of the first optical scanner 22) has a conjugate relationship to a position of the second optical scanner 24 (position of a scanning center of the second optical scanner 24). Note that in the present specification "conjugate relationship" is not limited to being a completely conjugate relationship, and instead means a conjugate relationship including pre-permitted errors for errors due to manufacturing, errors due to changes over the passage of time, and the like. Moreover, in the present specification an "afocal optical system" is not limited to a completely afocal optical system, and instead means an afocal optical system including pre-permitted errors for errors due to manufacturing, errors due to changes over the passage of time, and the like.

Explanation next follows regarding an outline of operation of the imaging optical system 19 configured as described above. A parallel beam of SLO light or OCT light introduced into the imaging optical system 19 passes through the combining section and is angle-scanned by the second optical scanner 24 configured by a polygon mirror or the like. The angle-scanned parallel beam of SLO light or OCT light is transmitted in sequence through the second lens group 296 and the first lens group 295, is angle-scanned by the first optical scanner 22, and a parallel beam of light is projected as is through the object optical system 28 onto the pupil plane of the examined eye 12 at a specific magnification, so as to perform angle-scanning with the pupil of the examined eye 12 as the scanning center. This parallel light beam is focused by the examined eye 12, and a focused spot of the SLO light or OCT light on the fundus of the examined eye 12 is scanned as illuminated light over the fundus. Reflected light obtained by this illuminated light being reflected by the fundus passes through the pupil of the examined eye 12, passes in sequence through the object optical system 28, the first optical scanner 22, the first lens group 295, the second lens group 296, the second optical scanner 24, the first lens group 295, the second lens group 296, the second optical scanner 24, and the combining section 26, and is then incident to the SLO unit 18 or the OCT unit 20. The respective behavior of reflected light after being incident to the SLO unit 18 or the OCT unit 20 is as described above.

The fixation section 29, which is an optical system for presenting a fixation target, is disposed between the first lens group 295 and the second lens group 296, which are in turn disposed between the first optical scanner 22 and the second optical scanner 24. The fixation section 29 includes a fixation light source 291 functioning as a fixation light, a fixation light scanner 292, a third lens group 293, and a reflection element 294 such as a half-mirror, in a configuration such that light from the fixation light source 291 (hereafter referred to as fixation light) is guided along the main optical axis AX of the imaging optical system 19. Moreover, the third lens group 293 in the fixation section 29 is disposed at a conjugate position in optical path length to the first lens group 295 and to the second lens group 296. The third lens group 293 also has a conjugate relationship to the position of the first optical scanner 22 (the position of the scanning center of the first optical scanner 22) and the position of the fixation light scanner 292 (the position of the scanning center of the fixation light scanner 292), so as to thereby configure an afocal optical system.

The first optical scanner 22 is an example of a "scanning optical system" and of a "second scanning optical system" of the present disclosure. The second optical scanner 24 is an example of a "first scanning optical system" of the present disclosure. The second optical scanner 24 is an example of an "optical scanner" of the present disclosure. The reflection element 294 is an example of an "optical member" of the present disclosure. The fixation light source 291 is an example of a "fixation light source" of present disclosure, and the fixation light scanner 292 is an example of a "fixation light scanning section" of the present disclosure. The fixation light scanner 292 is an example of a "fixation light scanner" of the present disclosure.

The fixation light scanner 292 of the fixation section 29 is controlled so as to be driven synchronized to the first optical scanner 22. The driving control of the fixation light scanner 292 is performed by the control device 16 (described in detail later).

As illustrated in FIG. 5, an illumination angle toward the examined eye 12 is changed by guiding the main optical axis of the fixation light with the fixation section 29 and scanning with the first optical scanner 22, such that the fixation target is moved in a horizontal direction. Thus in the present exemplary embodiment the fixation light scanner 292 is disposed and the fixation light scanner 292 is driven in synchronization with the first optical scanner 22 so that the fixation target is static (so as to eliminate any horizontal movement amount due to the H scanner 22). The fixation target is accordingly continuously illuminated at the same position with respect to the examined eye 12 even though the SLO light and the OCT light are being scanned by the first optical scanner 22 (H scanner for scanning in the horizontal direction). Namely, the fixation light from the fixation light source 291 is scanned by the fixation light scanner 292 in synchronization with the scanning of the first optical scanner 22 such that the fixation target from the fixation light source 291 does not move a specific distance or greater from the appropriate position with respect to the examined eye 12 due to scanning with the first optical scanner 22.

Figure 6:
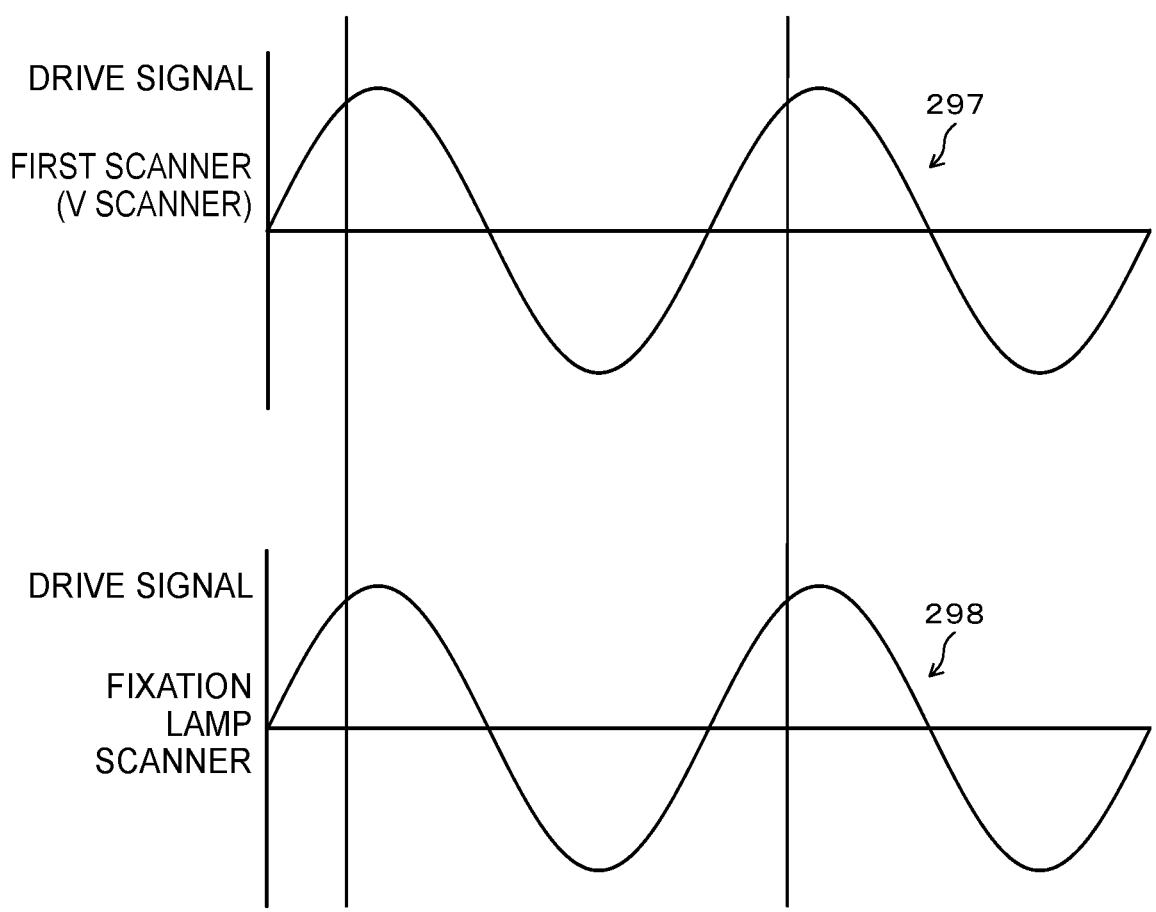
FIG. 6 is a characteristic chart illustrating an example of drive signals for a first scanner and for a third scanner of a fixation section.

Specifically, the fixation light scanner 292 is driven with an equivalent scanning angle to the scanning angle of the first optical scanner 22, but in the opposite direction to the scanning direction thereof. As illustrated in FIG. 5, when the first optical scanner 22 has been rotated (light has been scanned) in an arrow Ra direction, the fixation light scanner 292 is rotated in an arrow Rb direction. The fixation light moves over the reflection element 294 in an arrow Rc direction due to rotation of the fixation light scanner 292 in the arrow Rb direction. In such cases, the first optical scanner 22 and the fixation light scanner 292 are each synchronized driven with a common phase. Namely, as illustrated in FIG. 6, the control device 16 matches signal periods and phases for a drive signal 297 of the first optical scanner 22 and a drive signal 298 of the fixation light scanner 292 to respectively drive the first optical scanner 22 and the fixation light scanner 292 with the matched signal periods and phases. This means that the first optical scanner 22 and the fixation light scanner 292 are respectively driven in synchronization with a common fluctuation for the fluctuation in the rotation angle of the first optical scanner 22 and the fluctuation in the rotation angle of the fixation light scanner 292.

By synchronized driving of the first optical scanner 22 and the fixation light scanner 292 using common signal periods and common phases, even when there is a fluctuation in the scanning angle of scanning by the first optical scanner 22, the fixation light is introduced into the first optical scanner 22 at an angle cancelling out this fluctuation. The fixation target is accordingly static, the fixation light is illuminated onto the examined eye 12 at a given angle (for example, an angle formed between the gaze direction and the main optical axis AX), enabling orientation (gaze direction) of the examined eye 12 to be guided to a given direction of the illumination direction of the fixation light.

Taking the drive signal of the first optical scanner 22 as a first drive signal, and taking the drive signal of the fixation light scanner 292 as a second drive signal, then the same waveform or similar waveforms may be employed for the first drive signal and the second drive signal, or the second drive signal may have a waveform that is proportional to the first drive signal. Generating the first drive signal and the second drive signal in this manner means that there is a fixed total amount at the optical conjugative positions for the sum of light ray deflection by the first scanner and light ray deflection by the second scanner. Thus while the imaging light that is SLO light or OCT light is being scanned over the examined eye by the first optical scanner 22, the fixation target continues to be illuminated at a fixed position. The orientation of the examined eye 12 can accordingly be fixed while the imaging light that is SLO light or OCT light is being scanned over the examined eye 12.

Figure 7:
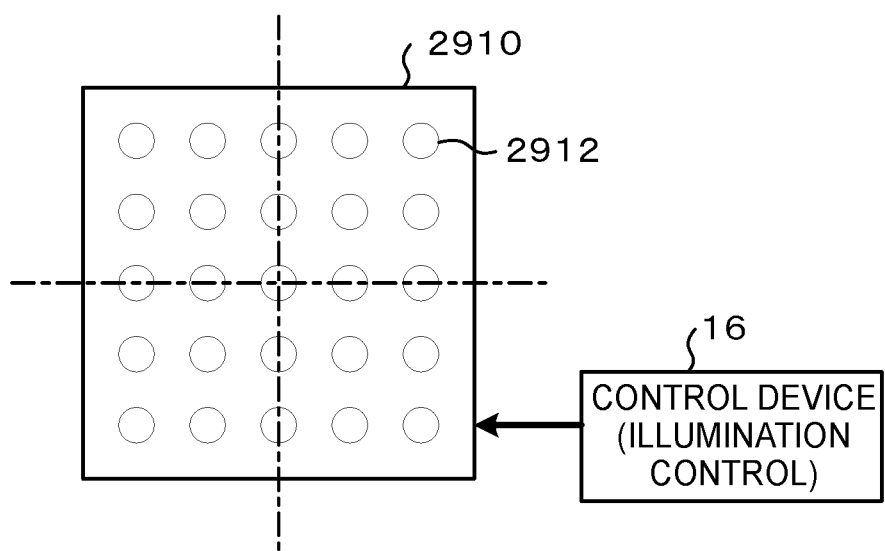
FIG. 7 is an explanatory diagram illustrating an example of a light source capable of changing fixation target positions where a fixation target is presented.
Figure 8:
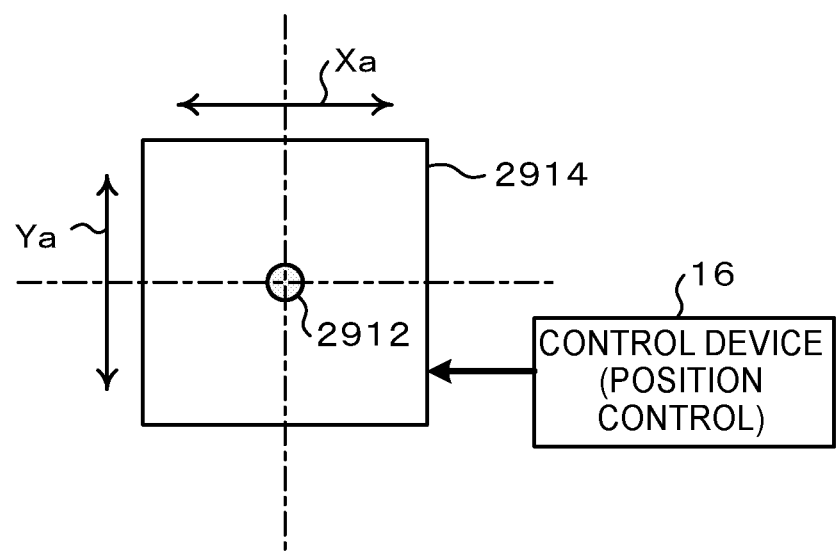
FIG. 8 is an explanatory diagram illustrating an example of a light source capable of changing fixation target positions where a fixation target is presented.

The fixation section 29 is configured capable of changing the position where the fixation target is presented. The control to change the position to present the fixation target is performed by the control device 16. FIG. 7 and FIG. 8 illustrate examples of configurations capable of changing the position where the fixation target is presented.

In the example illustrated in FIG. 7, the fixation section 29 includes a light source array 2910 of plural fixation lights 2912 to emit fixation light. The illumination of the light source array 2910 is controlled by the control device 16. The light emitting face of the light source array 2910 is placed conjugate to the retina of the examined eye 12. The position on the fixation light source 291 where the fixation light is emitted is a position changeable in two dimensions by one or other of the fixation light 2912 in the light source array 2910 being illuminated by the control device 16. Namely, control is performed to change the position where the fixation light is illuminated from a first position to a second position different to the first position. This enables the orientation of the examined eye to be changed with respect to the optical axis. When the fixation light is being illuminated at the first position, the imaging light that is SLO light or OCT light is scanned over a first region of the examined eye 12 enabling, for example, imaging to be performed of a center portion of the fundus (a fundus rear pole portion including the macular and the optical nerve head). When the position where the fixation light is being illuminated is at the second position, due to the examined eye 12 being orientated toward the second position, the illuminated light can be scanned over a second region of the examined eye 12 different to the first region (a region including a peripheral portion at a periphery to the center portion and including part of the center portion).

Moreover, in the example illustrated in FIG. 8, the fixation section 29 is equipped with a light source 2914 that includes a fixation light 2912, and is configured so as to be capable of moving in directions Xa along an X direction and capable of moving in directions Ya along a Y direction. The position of the light source 2914 is controlled by the control device 16. Changing the position of the light source 2914 by the control device 16 means the position where the fixation light is emitted in the fixation light source 291 (the position of the fixation light 2912) is a position changeable in two dimensions. This accordingly enables the orientation (gaze direction) of the examined eye 12 to be guided toward a given direction by changing the position where the fixation target is presented. In the present exemplary embodiment an example will be explained of a case in which the light source array 2910 illustrated in FIG. 7 is employed as the fixation light source 291.

Figure 9:
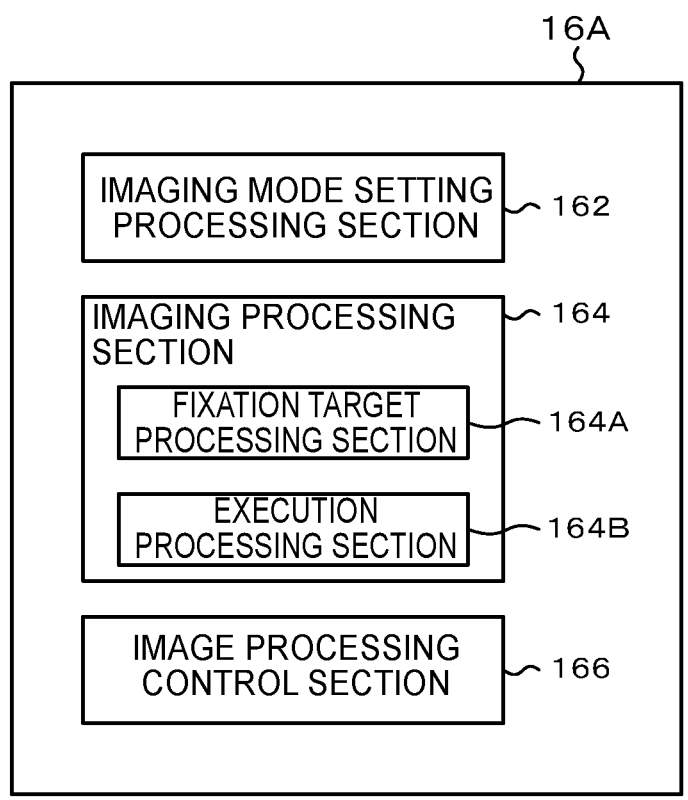
FIG. 9 is a block diagram illustrating an example of an imaging function of an ophthalmic device.

Next, description follows regarding an imaging function realized by the CPU 16A of the control device 16 of the ophthalmic device 110 executing an imaging processing program, with reference to FIG. 9. The imaging processing program includes an imaging mode setting processing function, an imaging processing function (fixation processing function, execution processing function), and an image processing control function. By the CPU 16A executing the imaging processing program including each of these functions, the CPU 16A functions as an imaging mode setting processing section 162, an imaging processing section 164 (fixation target processing section 164A, execution processing section 164B), and an image processing control section 166, as illustrated in FIG. 9. The imaging processing program is an example of a "program" of the present disclosure. A storage medium stored with the imaging processing program is an example of a "recording medium" of the present disclosure.

The imaging processing program is an example of a "program" of the present disclosure.

Figure 10:
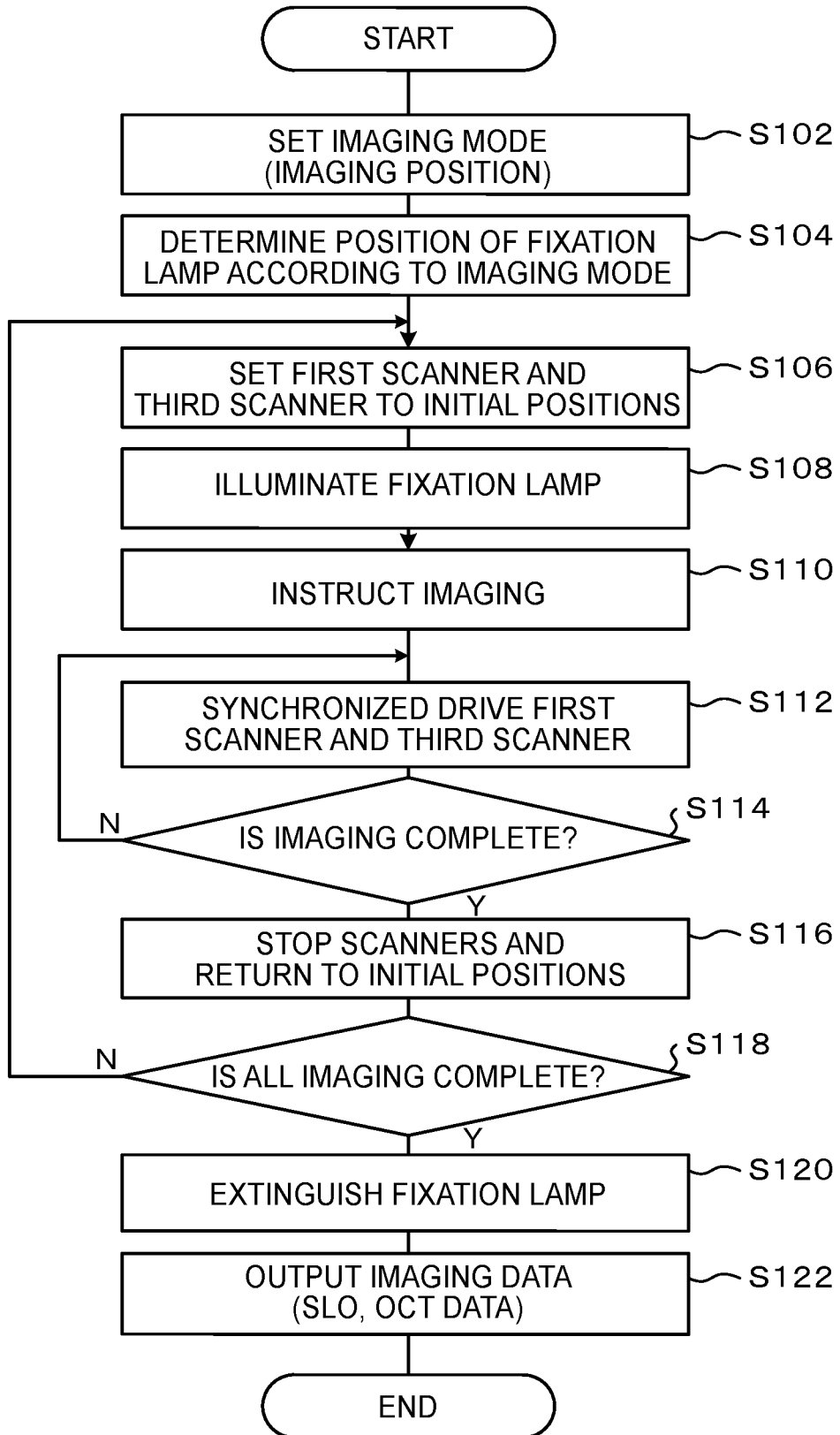
FIG. 10 is a flowchart illustrating an example of a flow of imaging processing.

Next, detailed description follows regarding imaging processing by the ophthalmic device 110, with reference to FIG. 10. Imaging processing as illustrated in the flowchart of FIG. 10 is implemented by the CPU 16A of the control device in the ophthalmic device 110 executing the imaging processing program. The imaging processing program is started when the start of imaging processing for the examined eye 12 is instructed by an operator operating the input-output/display device 16E of the ophthalmic device 110.

The imaging processing illustrated in the flowchart of FIG. 10 is an example of processing to implement a "control method of an ophthalmic device" of the present disclosure.

When the imaging processing program is started, at step S102, the imaging mode setting processing section 162 sets an imaging mode obtained by detecting operation of the input-output/display device 16E. The imaging mode indicates an imaging site and an imaging method for the examined eye 12. Examples thereof include an SLO imaging mode to image a posterior eye portion (for example the fundus) of the examined eye 12 using the SLO unit 18, and an OCT imaging mode to image a posterior eye portion of the examined eye 12 using the OCT unit 20. Note that the imaging mode is not limited to an imaging mode to image a posterior eye portion of the examined eye 12, and may include an imaging mode to image an anterior eye portion, and an imaging mode that performs imaging related to the examined eye 12. The imaging mode is set by the processing of step S102.

At step S104, the fixation target processing section 164A of the imaging processing section 164 executes fixation target position acquisition processing by acquiring a predetermined fixation target position for the already set imaging mode from a table. The table is information associating imaging modes with fixation target positions, and has been pre-stored in the ROM 16C. Note that the table may be acquired from an external device.

At step S106, the fixation target processing section 164A sets the first optical scanner 22 (H scanner) and the fixation light scanner 292 (third scanner) to predetermined initial positions (for example, positions in which each beam propagates in a direction along the main optical axis AX). At step S108, the fixation target processing section 164A performs control to illuminate the fixation light 2912 at a specific position on the light source array 2910 required to present the fixation target at the specific position acquired at step S104. The fixation target is thereby presented at the predetermined position corresponding to the imaging mode, and the orientation (gaze direction) of the examined eye 12 is guided so as to complete preparation.

At step S110, the execution processing section 164B executes (starts) imaging processing according to the imaging mode set at step S102.

At step S112, the fixation target processing section 164A performs control to drive the first optical scanner 22 (H scanner) and the fixation light scanner 292 (third scanner) in a synchronized manner. Namely, control is performed to match a drive signal 297 of the first optical scanner 22 with a drive signal 298 of the fixation light scanner 292 in both signal period and phase, and to respectively drive the first optical scanner 22 and the fixation light scanner 292 with the matched signal (FIG. 6). At step S114, the execution processing section 164B determines whether or not the imaging processing has been completed, and repeatedly executes the processing of step S112 until the processing has been completed (until affirmative determination is made at step S114). At step S116, at least the first optical scanner 22 (H scanner) and the fixation light scanner 292 (third scanner) are stopped and returned to their initial positions.

At step S118, the execution processing section 164B determines whether or not fixation target presentation and imaging processing has been completed for each of all the positions acquired at step S104. The execution processing section 164B returns processing to step S106 when not all of the processing has been completed (negative determination is made at step S118) and transitions processing to step S120 when all of the processing has been completed (affirmative determination is made at step S118).

At step S120, the fixation target processing section 164A extinguishes the fixation light source 291. Note that in the processing routine illustrated in FIG. 10, the fixation light source 291 is illuminated prior to imaging, and the fixation light source 291 is extinguished when imaging ends. The present disclosure is not limited to cases in which fixation light source 291 is illuminated during imaging. For example, in cases in which the fixation light from the fixation light source would affect imaging, the fixation light source may be extinguished immediately prior to imaging the eye. Moreover, the illumination of the fixation light source 291 is not limited to constant illumination, and includes a state of predetermined duration illumination, and a flickering state in which the state of predetermined duration illumination is repeated.

At step S122, the image processing control section 166 outputs image data. Specifically, image data of a fundus image obtained by imaging the fundus of the examined eye 12 with the ophthalmic device 110 (for example an UWF-SLO image) is transmitted from the ophthalmic device 110 to the server 140. Namely, the image processing control section 166 controls the image processing device 17, performs noise reduction processing and the like to eliminate noise from the image obtained by imaging, performs image processing on the UWF-SLO image and UWF-OCT image, and then transmits these to the server 140.

In the server 140, after image data of the fundus image from imaging the fundus of the examined eye 12 using the ophthalmic device 110 (for example an UWF-SLO image) has been received from the ophthalmic device 110, the CPU 262 executes the image processing program so as to execute image processing.

Specifically, the server 140 uses the image processing control section 206 to acquire a fundus image configured from image data, performs specific image processing on the acquired fundus image, and generates a post-processing image on which the image processing has been performed. An example of the specific image processing is image processing to generate a combined image (see FIG. 11 and FIG. 12) in which plural UWF-SLO images, each imaged with the fixation target presented at a different position, have been combined.

For example, a combined image is generated in which at least two fundus images have been combined from out of fundus images IG1, IG2, IG3. Fundus image IG1 is a UWF-SLO image imaged when the fixation target was being presented at a fundus conjugate position Fcj on the main optical axis AX. The fundus images IG2 and IG3 are UWF-SLO images that were imaged when the fixation target was being presented at fundus conjugate positions Fcj positioned away from the main optical axis AX. Specifically, the fundus image IG2 is a UWF-SLO image that was imaged when the fixation target was being presented above the main optical axis AX, and the fundus image IG3 is a UWF-SLO image that was imaged when the fixation target was being presented below the main optical axis AX.

The server 140 performs image processing such as pattern matching on the fundus images IG2 and IG3 so as, for example, to match blood vessel portions with reference to the fundus image IG1, then performs image processing to combine the fundus images IG2 and IG3 therewith and generate the post-processing image.

The processing section 208 stores each of the fundus images, and also stores the post-processing image (combined image), together with information about the patient (patient ID, name, age, visual acuity, a right eye/left eye discriminator, eye axial length, and the like), in the storage device 254 (see FIG. 3).

The display control section 204 may also display the post-processing image on the display 256.

A patient ID is input to the viewer 150 when an ophthalmologist is examining the examined eye 12 of the patient. The viewer 150 that has been input with the patient ID then instructs the server 140 to transmit the patient information corresponding to that patient ID, together with the image data of each image (IG1, IG4 and the like). The viewer 150, on receiving the patient information together with the image data of each image (IG1, IG4) generates a diagnosis screen 400 for the examined eye 12 of the patient, as illustrated in FIG. 11, to be displayed on a display of the viewer 150.

Figure 11:
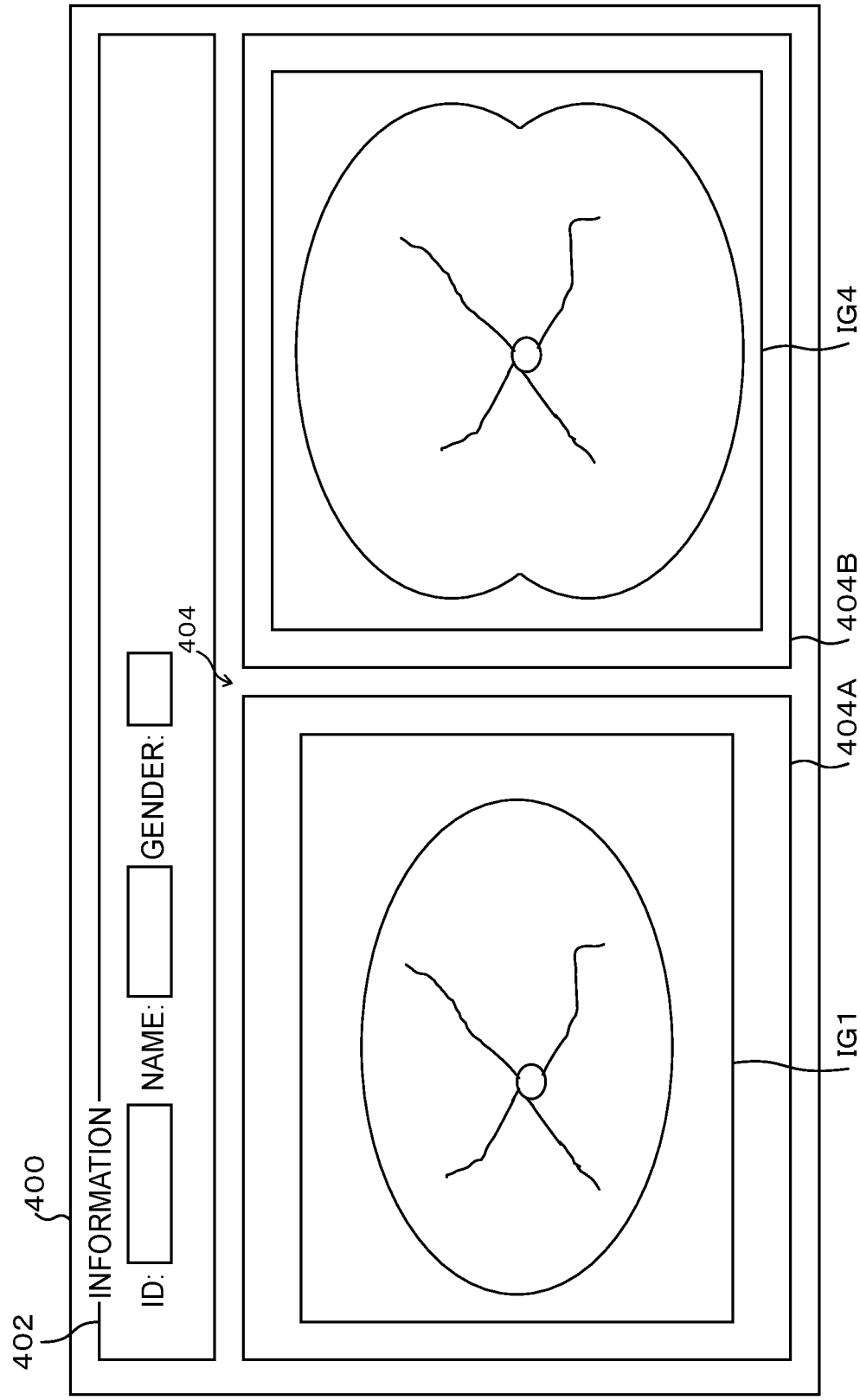
FIG. 11 is an image illustrating an example of a diagnostic screen of a viewer.

FIG. 11 illustrates the diagnosis screen 400 of the viewer 150. As illustrated in FIG. 11, the diagnosis screen 400 includes an information display region 402 and an image display region 404.

Information related to the patient, such as the patient ID, patient name, patient gender, etc., is displayed in the information display region 402. Note that although omitted in the drawing, various information such as information indicating the patient's age, visual acuity, information indicating whether the image being displayed in the right eye or the left eye, the eye axial length, and the like, may also be displayed in the information display region 402. Based on the received patient information, the viewer 150 displays information related to the corresponding patient in the information display region 402.

The image display region 404 includes a main image display region 404A and a combined image display region 404B. Based on the received image data, the viewer 150 displays corresponding images (the fundus image IG1 as the main image, and the fundus image IG4 as the combined image) in each of the image display regions (404A, 404B). Although omitted in the drawing, the year, month, and day of the day imaging was performed, which is the day the image being displayed was acquired, may also be displayed in each of the image display regions 404A, 404B.

Figure 12:
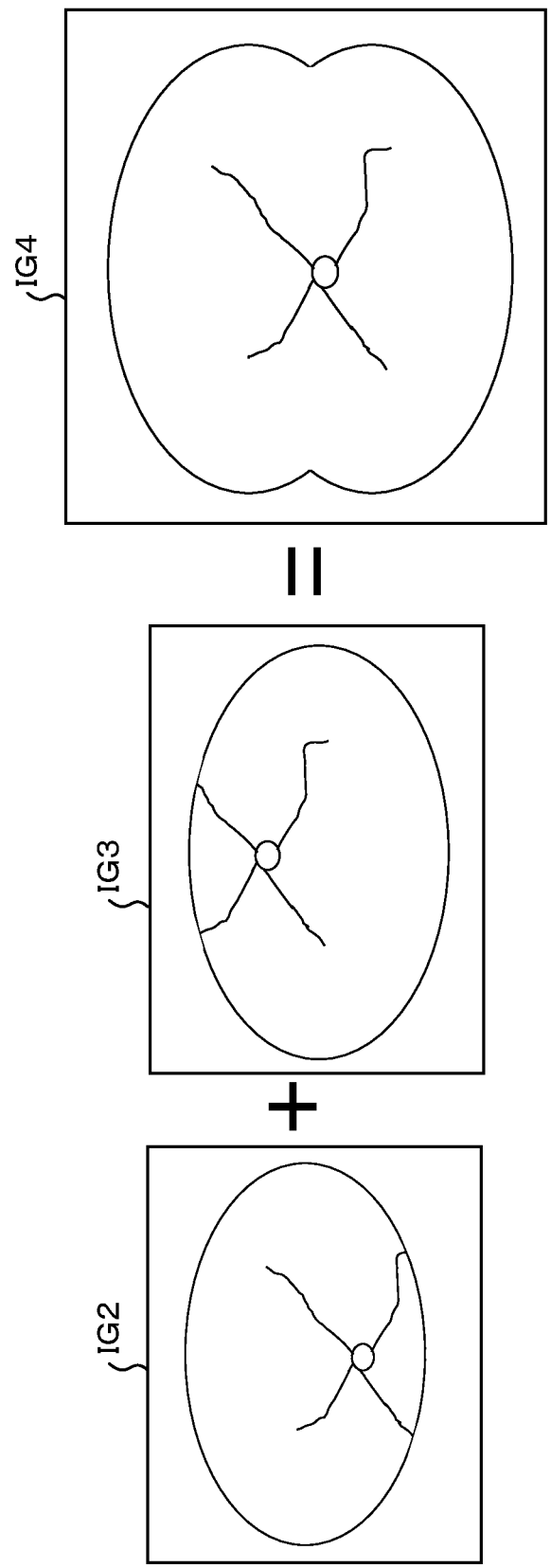
FIG. 12 is an explanatory diagram to explain a combined image generated from fundus images.

The combined image of the fundus image IG4 is, as illustrated in FIG. 12, an image in which the fundus image IG2 imaged when fixating upward and the fundus image IG3 imaged when fixating downward have been combined using pattern matching or the like to match blood vessel portions therein with reference to the fundus image IG1.

Note that a text display region for displaying text information related to the images may also be included in the image display region 404. An example of such text information is, for example, text information such as "The fundus image being displayed in the region on the left is from when the fixation target was being presented on the main optical axis AX. The image being displayed in the region on the right is an image that combines respective fundus images from when the fixation target was being respectively presented above and below".

Furthermore, although various information useful for diagnosis may be displayed on the diagnosis screen 400, this information is omitted in the example illustrated in FIG. 11.

By synchronized driving of the first optical scanner 22 and the fixation light scanner 292 using common signal periods and common phases in this manner, even when there is a fluctuation in the scanning angle for scanning with the first optical scanner 22, the fixation light is still introduced into the first optical scanner 22 at an angle cancelling out this fluctuation. The fixation target is accordingly static, and the fixation light is illuminated onto a given position on the examined eye 12 (for example, a position to achieve a gaze direction along the main optical axis AX), enabling the orientation (gaze direction) of the examined eye 12 to be guided toward a given direction.

The fixation section 29 described above has been explained for a case in which the illumination position of the fixation light source is controlled using the light source array 2910 (FIG. 7) as the fixation light source 291, however the present disclosure is not limited thereto. For example, instead of changing the illumination position of the fixation light source, a configuration may be adopted in which an offset is applied to the drive signal of the scanners performing synchronized driving. Cases in which the drive signal is offset are described as a first modified example.

Figure 13:
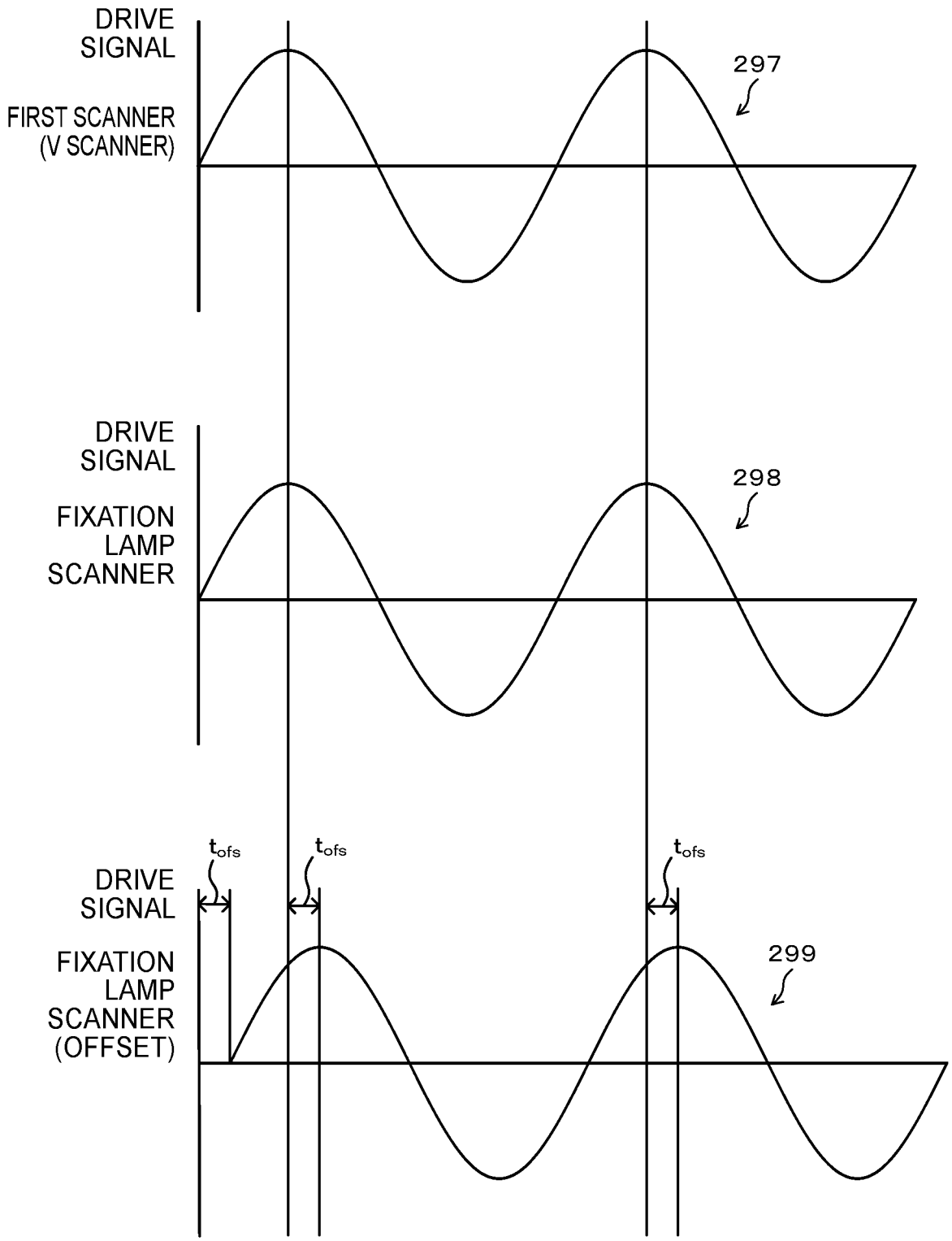
FIG. 13 is a characteristic chart illustrating an example of drive signals in a first modified example.

As illustrated in FIG. 13, in the above description, the drive signal 297 of the first optical scanner 22 and the drive signal 298 of the fixation light scanner 292 are matched in both signal periods and phases, and respectively drive the first optical scanner 22 and the fixation light scanner 292. In contrast thereto, a configuration is adopted in which the fixation light scanner 292 is driven by a drive signal 299 that has been offset by a specific offset time tofs. The offset time tofs may be determined by a scanning time of a scanning angle of the first optical scanner 22 corresponding to a position where the fixation target is presented away from a case in which common driving is performed with an offset time "0". The fluctuation in the rotation angle of the first optical scanner 22 and the fluctuation in the rotation angle of the fixation light scanner 292 are synchronized to a common fluctuation by offsetting with the offset time tofs and then respectively driving the first optical scanner 22 and the fixation light scanner 292. The fixation target is accordingly static at the offset position, the fixation light is illuminated at a given position offset on the examined eye 12, enabling the orientation (gaze direction) of the examined eye 12 to be guided toward the direction of offset.

Moreover, the fixation target may be presented at positions changeable in two dimensions in cases in which the fixation light is illuminated offset with respect to the drive signal 297 of the first optical scanner 22.

Figure 14:
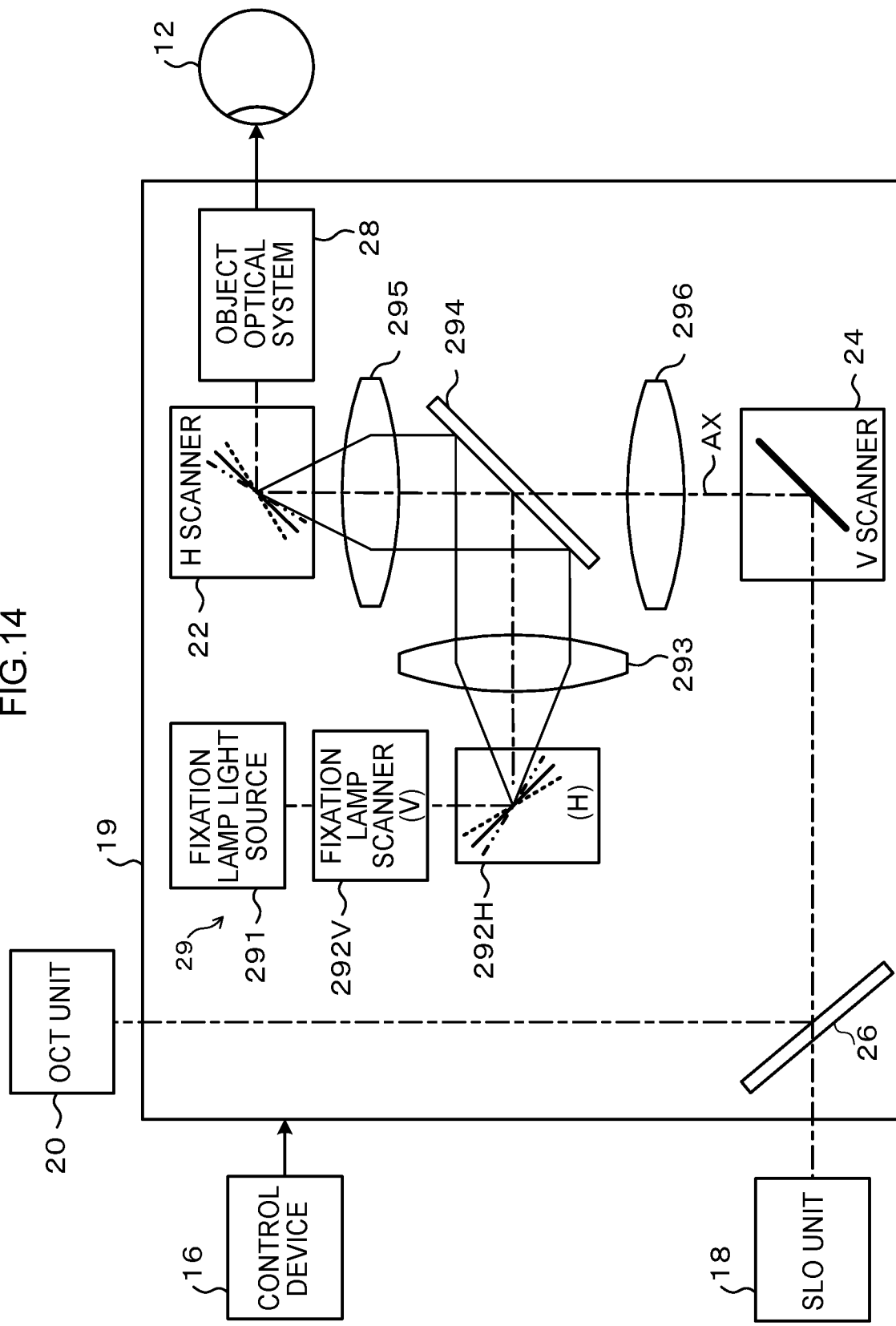
FIG. 14 is a schematic diagram illustrating an example of a configuration to present a fixation target in the first modified example.

FIG. 14 is a schematic diagram illustrating an example of a configuration in cases in which the fixation target is presented at positions changeable in two dimensions.

As illustrated in FIG. 14, the fixation section 29 includes a first fixation light scanner 292V to scan fixation light in one direction, and a second fixation light scanner 292H to scan the fixation light in a direction intersecting (for example orthogonal to) that of the first fixation light scanner 292V. The second fixation light scanner 292H is, similarly to the fixation light scanner 292, synchronized-driven (or offset-driven) with respect to the first optical scanner 22 (H scanner). The first fixation light scanner 292V has a configuration driven by a drive signal with a specific scanning angle offset from an initial position to a specific position in a direction intersecting with the scanning axis of the second fixation light scanner 292H. The specific scanning angle for offset in the second fixation light scanner 292H may be determined by a scanning time determined from a position on the first optical scanner 22 corresponding to a position where the fixation target is presented from a case in which common driving at the initial values is performed. Scanning with the first fixation light scanner 292V and the second fixation light scanner 292H in this manner enables the presentation position of the fixation target to be a position changeable in two dimensions.

The configuration for offset scanning performed by the fixation light scanner 292 described above by the specific offset time tofs, and the first fixation light scanner 292V and the second fixation light scanner 292H are examples of a "change section" of the present disclosure.

Attenuation of light for illumination of the fundus with the SLO light or the OCT light, and attenuation of the reflected light reflected by the fundus, is preferably suppressed. The attenuation of light by the reflection element 294 of the fixation section 29 is accordingly preferably reduced by as much as possible. A configuration in which light attenuation by the reflection element 294 of the fixation section 29 is reduced by as much as possible will accordingly be described as a second modified example, with reference to FIG. 15.

Figure 15:
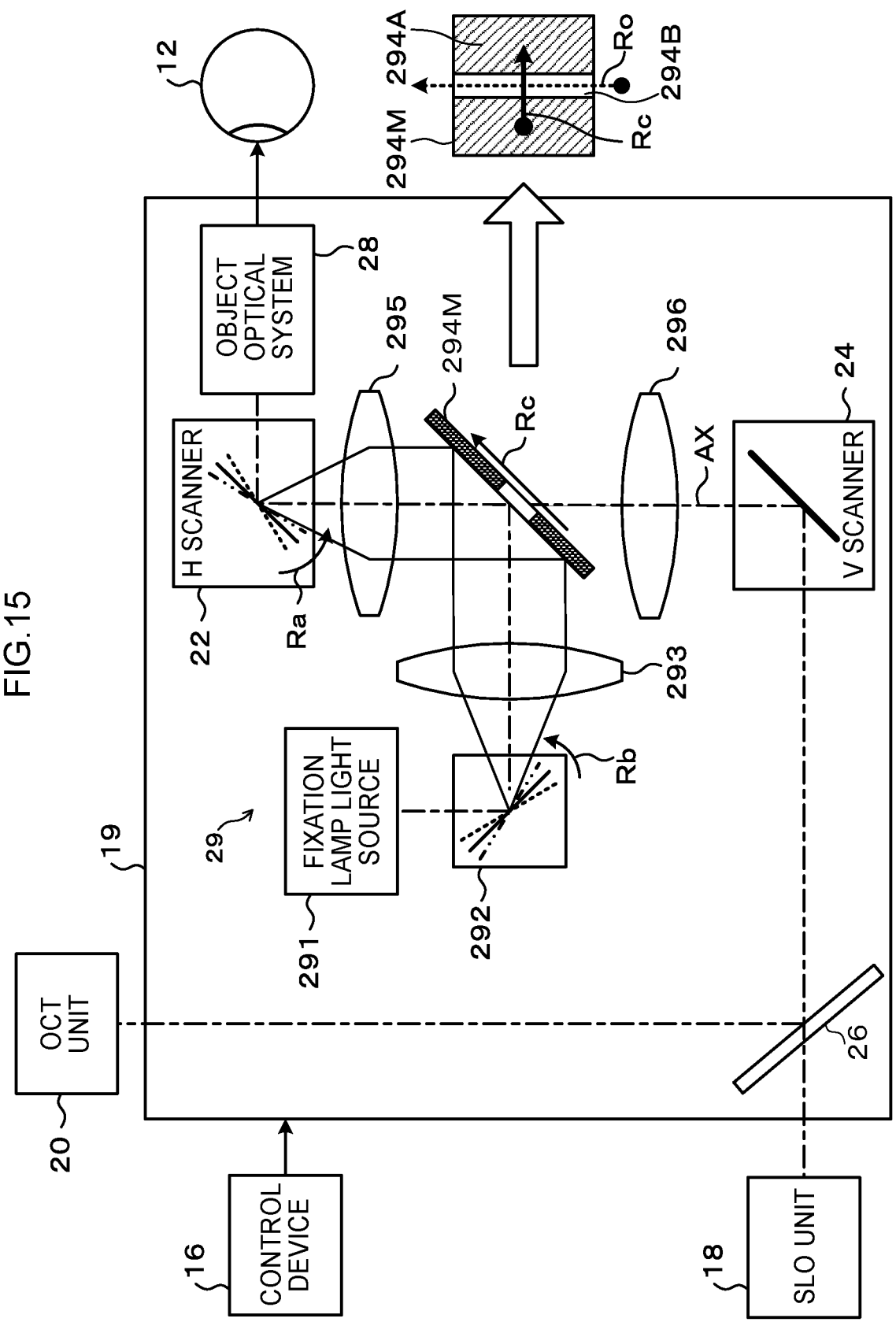
FIG. 15 is a schematic configuration diagram for a second modified example.

FIG. 15 is a schematic configuration diagram of the second modified example. As illustrated in FIG. 15, the imaging optical system 19 of the second modified example includes a particular reflection element 294M instead of the reflection element 294 illustrated in FIG. 5. The particular reflection element 294M is configured from a reflection region 294A to reflect the fixation light, and a transmission region 294B including at least a scanning range of the SLO light or the OCT light by the scanning the second optical scanner 24 (scanning in a direction indicated by arrow Ro). Adopting such a configuration in which the particular reflection element 294M is equipped with the transmission region 294B, enables light attenuation of the SLO light or the OCT light to be reduced when being transmitted through the particular reflection element 294M.

Note that the fixation light is scanned so as to move across both the reflection region 294A and the transmission region 294B by scanning with the fixation light scanner 292 (scanning in a direction indicated by arrow Rc). Thus in cases in which the fixation light passes through the transmission region 294B, the fixation light is not illuminated onto the examined eye and a momentary extinguished state arises, and the fixation target is presented in a flickering state. The momentary extinguished state of the fixation light endures for the time taken to pass through a portion of the scanning range using the fixation light scanner 292. Considering the residual image phenomenon in the examined eye 12, the extinguished time of the fixation light as it appears to the examined eye 12 is anticipated to be shorter than the time for the fixation light to pass through the transmission region 294B.

Moreover, in cases in which imaging processing is being performed with the SLO unit 18, the visible SLO light passes through the transmission region 294B while the fixation light is in the momentary extinguished state, and so the fixation target is presented in a state that appears close to a state in which the fixation light is being continuously illuminated. However, in cases in which imaging processing is being performed with the OCT unit 20, the visible SLO light is illuminated while the fixation light is passing through the transmission region 294B, enabling the fixation target to be presented in a state that appears close to a state in which the fixation light is being continuously illuminated.

Examples of applications of the present disclosure will now be given. Examples of applications include employing the function of illuminating light through the first optical scanner 22 while making the optical axis static with respect to the examined eye 12 in a device other than an ophthalmic device, by providing a scanner that is synchronized-driven with the first optical scanner 22 in the application example. Note that in the following application examples, configuration similar to that of the exemplary embodiment described above is appended with the same reference numerals for similar portions, and detailed explanation thereof will be omitted.

Generally imaging and examining an anterior eye portion of the examined eye 12 is effective when examining an examined eye. However, in imaging an anterior eye portion of the examined eye 12, a complicated optical system is required for the placement of the examination device at a position nearer to the examined eye 12 side than the first optical scanner 22 in order to exclude the effects of scanning by the first optical scanner 22. However, adopting a configuration as described above in which the particular scanner (the fixation light scanner 292) synchronized-driven with the first optical scanner 22 is provided enables a configuration to be realized in which the optical axis is made static with respect to the examined eye 12 even for a particular optical system through the first optical scanner 22. An examination device to examine the examined eye 12 is thereby able to examine the examined eye 12 simply due to the function of the fixation section 29 described above being employed. Moreover, being able to place the examination device on the optical path through the first optical scanner 22 increases the degrees of freedom for device design.

A first application example is application to an anterior eye portion imaging device, serving as an example of an examination device, of the function of making the optical axis of a fixation light illuminated onto the examined eye 12 static even when fixation light is illuminated through the first optical scanner 22 by providing a scanner synchronized-driven with the first optical scanner 22.

Figure 16:
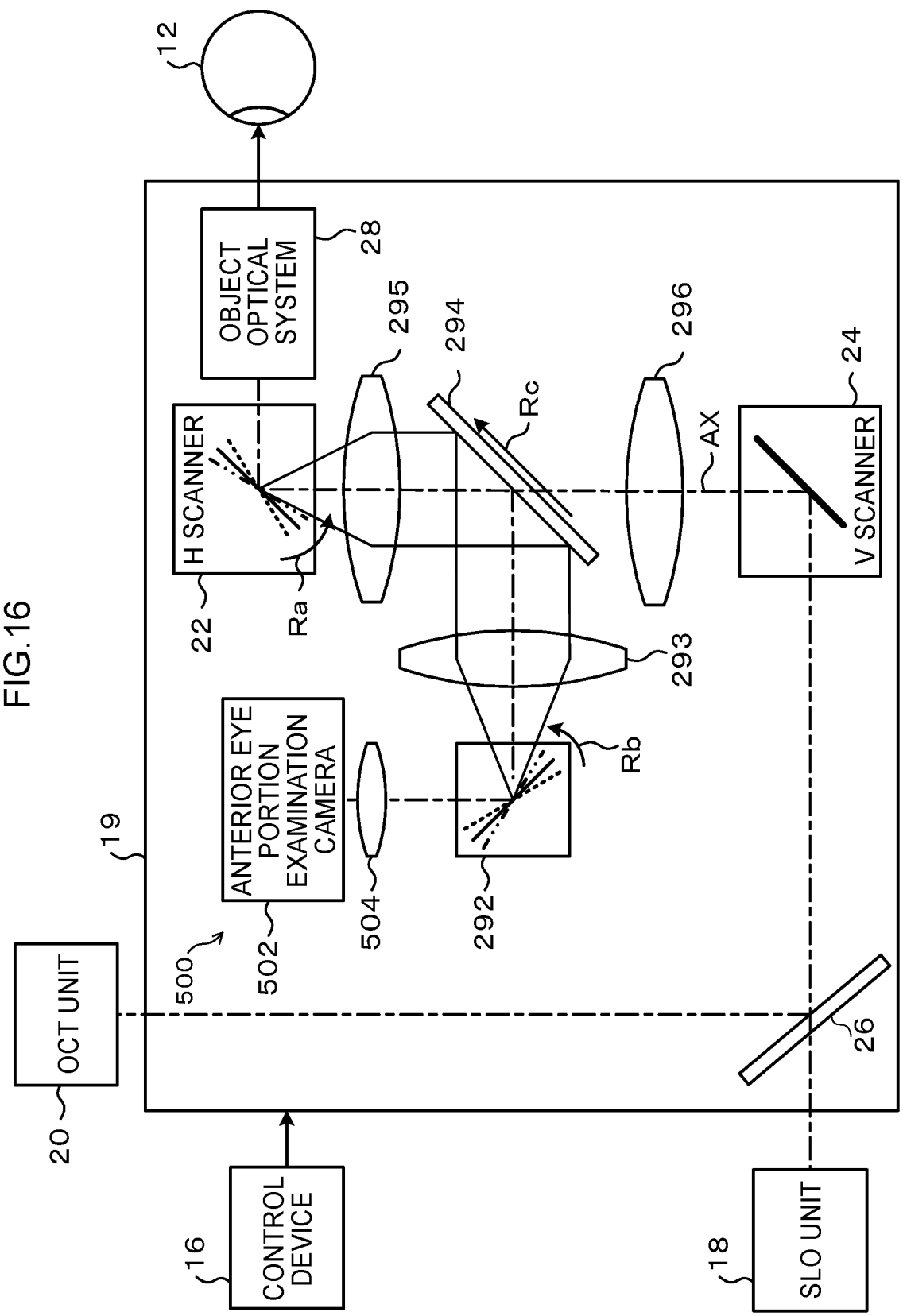
FIG. 16 is a schematic diagram illustrating an example of a configuration of a first application example.

FIG. 16 is a schematic illustration of a configuration of a first application example. As illustrated in FIG. 16, the first application example is an application example that, instead of the fixation light source 291 of the fixation section 29 (FIG. 5), has an anterior eye portion examination optical system 500 disposed therein that includes an anterior eye portion examination camera 502 and an anterior eye portion examination lens group 504. The imaging plane of the anterior eye portion examination camera 502 of the anterior eye portion examination optical system 500 is disposed with a conjugate relationship to the pupil (pupil 27) of the examined eye 12.

As illustrated in FIG. 16, by disposing the anterior eye portion examination optical system 500 instead of the fixation light source 291 (FIG. 5), a static position can be achieved for the position from which to examine the anterior eye portion of the examined eye 12, enabling stable examination of the anterior eye portion of the examined eye 12.

The following disclosed technology is proposed in the first application example.

An ophthalmic device including a scanning optical system configured to scan an eye using light from a light source, and an examination section configured to examine the eye through the scanning optical system. The examination section is configured to change an optical axis for examining the eye in synchronization with scanning with the scanning optical system such that for a predetermined site on the eye, the optical axis does not move a specific distance or greater from the predetermined site on the eye due to the scanning of the scanning optical system.

A second application example is an application example in which the imaging optical system 19 according to the above exemplary embodiment (FIG. 5) is further equipped with an anterior eye portion imaging device. The second application example has functionality that is effective in cases in which the examined eye 12 is being examined while a fixation target is being presented.

Figure 17:
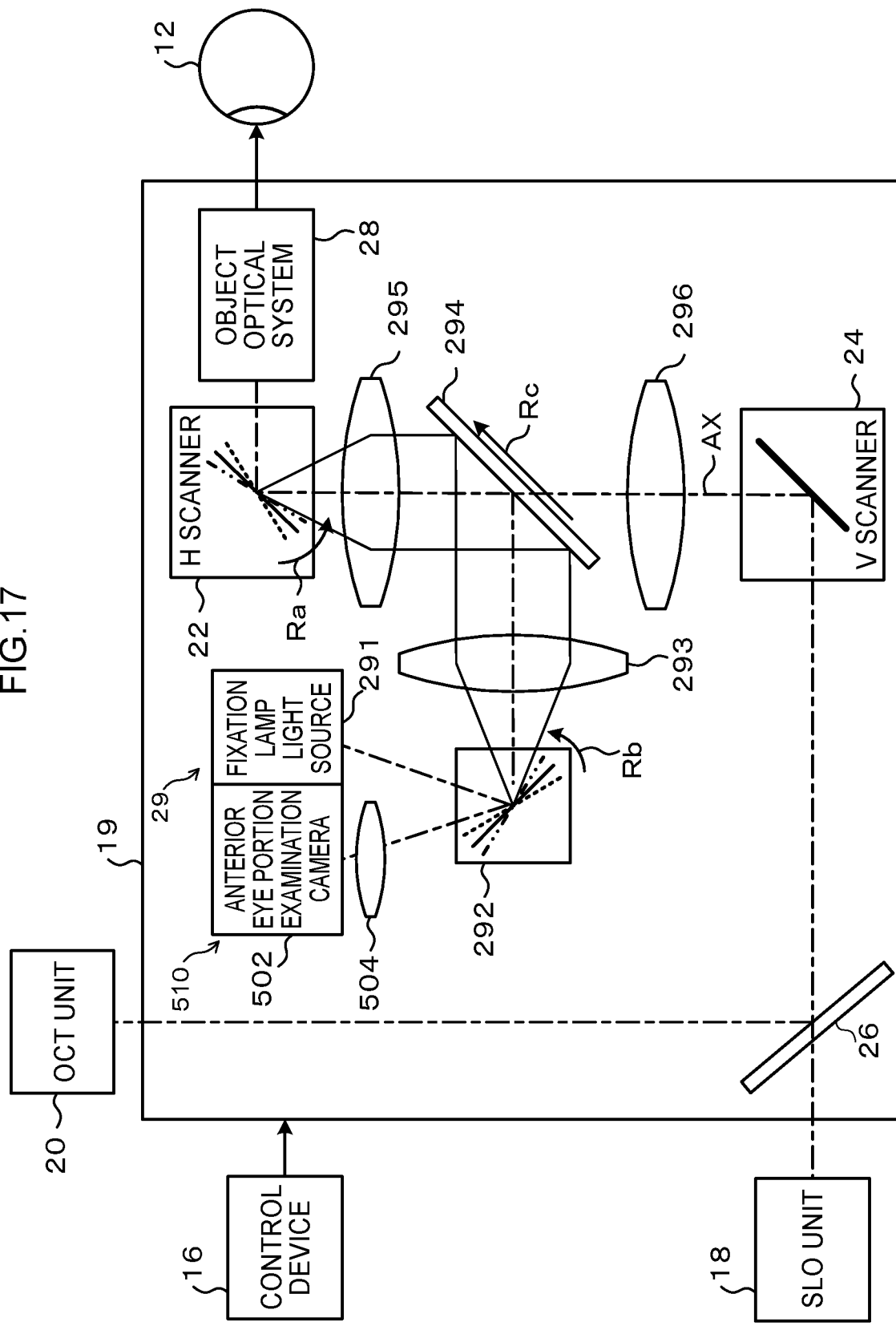
FIG. 17 is a schematic diagram illustrating an example of a configuration of a second application example.

FIG. 17 schematically illustrates a configuration of the second application example. As illustrated in FIG. 17, in the second application example the imaging optical system 19 equipped with the fixation section 29 (FIG. 5) described above has an anterior eye portion examination optical system 510 further disposed therein. Note that the anterior eye portion examination optical system 510 illustrated in FIG. 17 has a configuration similar to the anterior eye portion examination optical system 500 illustrated in FIG. 16, and description thereof will be omitted.

As illustrated in FIG. 17, the imaging optical system 19 according to the second application example enables an anterior eye portion of the examined eye 12 to be imaged and examined while presenting a fixation target using the fixation section 29. Namely, by disposing the anterior eye portion examination optical system 510 in addition to the fixation section 29 (FIG. 5), even in cases in which the optical path of the anterior eye portion examination optical system 510 is through the first optical scanner 22, the position from which to examine the anterior eye portion of the examined eye 12 can be made static, enabling stable examination of the anterior eye portion of the examined eye 12.

In the second application example the following disclosed technology is proposed.

An ophthalmic device including a scanning optical system, a fixation light source, a fixation light scanning section, and an examination section. The scanning optical system is configured to scan an eye with light from a light source. The fixation light source is configured to illuminate fixation light onto the eye through the scanning optical system so as to function as a fixation target. The fixation light scanning section is configured to scan the fixation light in synchronization with scanning of the scanning optical system such that fixation light illuminated from the fixation light source onto a predetermined site on the eye does not move a specific distance or greater from the predetermined site on the eye due to the scanning of the scanning optical system. The examination section is configured to examine the eye through the scanning optical system. The examination section is also configured to change an optical axis for examining the eye in synchronization with scanning with the scanning optical system using the fixation light scanning section such that for a predetermined site on the eye, the optical axis does not move a specific distance or greater from the predetermined site on the eye due to the scanning of the scanning optical system.

A third application example is an application in which the function to make an optical axis of a fixation light for illuminating the examined eye 12 static is applied to a perimeter that is an example of fixed lighting.

Figure 18:
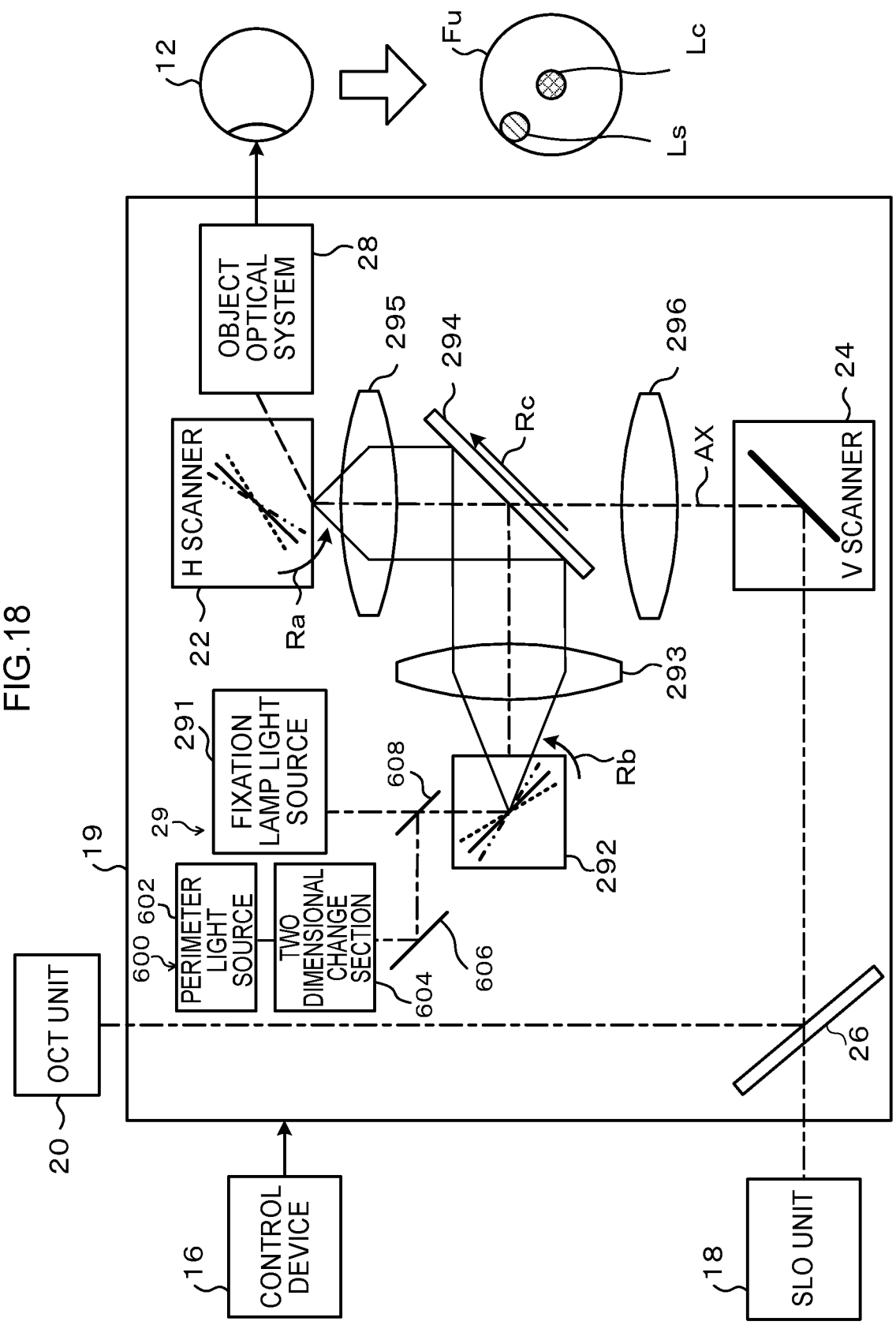
FIG. 18 is a schematic diagram illustrating an example of a configuration of a third application example.

FIG. 18 schematically illustrates a configuration of the third application example. The third application example is the imaging optical system 19 equipped with the fixation section 29 (FIG. 5) described above, further disposed with a perimeter optical system 600. As illustrated in FIG. 18, the perimeter optical system 600 is equipped with a perimeter light source 602, a two dimensional change section 604, a mirror 606, and a mirror 608 provided on the optical path of the fixation section 29.

The perimeter light source 602 is a light source having a configuration similar to that of the fixation light source 291. The two dimensional change section 604 is configured so that light from the perimeter light source 602 is changeable in two dimensions so as to be able to move a light spot Ls issuing from the perimeter light source 602 within a predetermined measurement range over a fundus (retina) Fu of the examined eye 12. The mirror 606 and the mirror 608 are arranged in this sequence at the light emission side of the two dimensional change section 604. Adopting such a configuration for the perimeter optical system 600 enables light employed for field of view measurements of the examined eye 12 to be shone two dimensionally across the fundus. For example, as illustrated in FIG. 18, this enables a light spot Lc from illumination of the fixation light to be shone onto the fundus Fu of the examined eye 12, and the light spot Ls from the perimeter light source 602 to be shone onto the fundus Fu of the examined eye 12 at a different position to the light spot Lc.

Thus in the third application example, using the perimeter optical system 600, field of view measurement light is able to be illuminated onto the fundus of the examined eye 12 while being changed two dimensionally, enabling the field of view range of the examined eye 12 to be measured while at the same time presenting the fixation target at a fixed position through illumination of the fixation light using the fixation section 29.

In the third application example the following disclosed technology is proposed.

An ophthalmic device including a scanning optical system, a fixation light source, a fixation light scanning section, and a change section. The scanning optical system is configured to scan an eye with light from a light source. The fixation light source is configured to illuminate fixation light onto the eye through the scanning optical system so as to function as a fixation target. The fixation light scanning section is configured to scan the fixation light in synchronization with scanning of the scanning optical system such that fixation light illuminated from the fixation light source onto a predetermined site on the eye does not move a specific distance or greater from the predetermined site on the eye due to scanning of the scanning optical system. The change section is included in a measurement section for measuring a field of view of the eye through the scanning optical system, and the control section is configured to change an optical axis for measuring the field of view of the eye in synchronization with the scanning of the scanning optical system using the fixation light scanning section such that for a predetermined site on the eye, the optical axis does not move a specific distance or greater from the predetermined site on the eye due to the scanning of the scanning optical system.

Note that although the ophthalmic device 110 described above has, for example, a function to perform imaging over a region having an internal illumination angle of 200° with respect to a reference position an eyeball center O of the examined eye 12 (an external illumination angle of 167° with respect to the pupil of the eyeball of the examined eye 12), there is no limitation to these angles of view. The internal illumination angle may be 200° or greater (the external illumination angle may be from 167° to 180°).

Moreover, a specification may be adopted in which the internal illumination angle is less than 200° (the external illumination angle is less than 167°). For example, angles of about 180° for the internal illumination angle (about 140° for the external illumination angle), about 156° for the internal illumination angle (about 120° for the external illumination angle), about 144° for the internal illumination angle (about 110° for the external illumination angle), and the like may be adopted as the angles of view. These numerical values are merely examples thereof.

Although explanation has been given in the exemplary embodiments described above regarding a case in which a computer is employed to implement data processing by software, the present disclosure is not limited thereto. For example, instead of software employing a computer, the various types of processing may be executed solely by hardware such as a field programmable gate array (FPGA) or an application specific integrated circuit (ASIC). Alternatively, a configuration may be adopted in which some processing out of the various types of processing is executed by a software, and the remaining processing is executed by hardware.

Moreover, in each of the examples described above, a processor has the broad meaning of processor, which encompasses general purpose processors (for example, a central processing unit (CPU) and the like), as well as dedicated processors (for example, a graphics processing unit (GPU), an application specific integrated circuit (ASIC), a field programmable gate array (FPGA), a programmable logic device, and the like).

Moreover, the processor actions in the exemplary embodiments described above are not necessarily performed by a single processor alone, and may be performed by the inter-cooperation of plural processor present at separated physical positions. Moreover, the sequence of each of the processor actions is not limited to the sequence given, and the sequence may be rearranged as appropriate.

What is claimed is:

1. An ophthalmic device comprising:
an imaging light source configured to image a fundus image of an examined eye;

a fixation light source configured to illuminate a light onto the examined eye so as to function as a fixation target to guide a gaze direction of the examined eye, when imaging the fundus image of the examined eye;

a first light scanning section configured to rotate at a predetermined speed in a first direction and scan light from the fixation light source; and a second light scanning section configured to rotate at a predetermined speed in a second direction and scan light from the fixation light source, and light from the fixation light source that has passed through the first light scanning section;

wherein the first light scanning section is configured to scan in synchronization with rotating of the second light scanning section in the second direction, and scan the light from the fixation light source, rotating in the first direction, to eliminate movement of the fixation target on the examined eye due to scanning of the second light scanning section.

2. The ophthalmic device of claim 1, further comprising a changing section configured to change at least one of a position or an illumination direction of the fixation light so as to transition a position of the fixation target with respect to the examined eye from a first position such that a fixation target is illuminated at a second position that is different from the first position.

3. The ophthalmic device of claim 1, further comprising a control section configured to control the fixation light source and the fixation light scanning section, based on instruction information indicating an instruction to guide an orientation of the examined eye in such a manner that a fixation target is illuminated at a position corresponding to the instruction.

4. The ophthalmic device of claim 1, further comprising an imaging section configured to image the examined eye.

5. The ophthalmic device of claim 1, further comprising:

a third light scanning section configured to rotate in a third direction intersecting the second direction, and scan a light from the imaging light source; and an optical member configured to transmit light from the imaging light source that has passed through the third light scanning unit, and reflect light from the fixation light source.

* * * * *